(12) United States Patent
Chen et al.

(10) Patent No.: US 9,522,918 B2
(45) Date of Patent: Dec. 20, 2016

(54) PHARMACEUTICAL COMPOSITIONS COMPRISING PERILLYL ALCOHOL DERIVATIVES

(71) Applicant: NEONC TECHNOLOGIES INC., Los Angeles, CA (US)

(72) Inventors: Thomas Chen, La Canada, CA (US); Daniel Levin, La Canada, CA (US); Satish Pupalli, Rancho Cucamonga, CA (US)

(73) Assignee: NeOnc Technologies, Inc., Los Angeles, CA (US)

( * ) Notice: Subject to any disclaimer, the term of this patent is extended or adjusted under 35 U.S.C. 154(b) by 0 days.

(21) Appl. No.: 15/041,743

(22) Filed: Feb. 11, 2016

(65) Prior Publication Data

US 2016/0237092 A1    Aug. 18, 2016

Related U.S. Application Data

(60) Provisional application No. 62/115,396, filed on Feb. 12, 2015.

(51) Int. Cl.
C07D 487/04    (2006.01)

(52) U.S. Cl.
CPC .................. C07D 487/04 (2013.01)

(58) Field of Classification Search
None
See application file for complete search history.

(56) References Cited

U.S. PATENT DOCUMENTS

| | | | |
|---|---|---|---|
| 4,353,365 A | 10/1982 | Hallworth et al. |
| 4,524,769 A | 6/1985 | Wetterlin |
| 4,738,851 A | 4/1988 | Schoenwald et al. |
| 4,882,150 A | 11/1989 | Kaufman |
| 5,035,237 A | 7/1991 | Newell |
| 5,077,033 A | 12/1991 | Viegas et al. |
| 5,225,183 A | 7/1993 | Purewal et al. |
| 5,239,993 A | 8/1993 | Evans |
| 5,403,841 A | 4/1995 | Lang et al. |
| 5,415,162 A | 5/1995 | Casper et al. |
| 5,521,222 A | 5/1996 | Ali et al. |
| 5,587,402 A | 12/1996 | Gould et al. |
| 5,602,184 A | 2/1997 | Myers et al. |
| 5,698,219 A | 12/1997 | Valdivia et al. |
| 5,715,810 A | 2/1998 | Armstrong et al. |
| 5,776,445 A | 7/1998 | Cohen et al. |
| 5,800,807 A | 9/1998 | Hu et al. |
| 5,874,063 A | 2/1999 | Briggner et al. |
| 5,983,956 A | 11/1999 | Trofast |
| 6,006,745 A | 12/1999 | Marecki |
| 6,056,950 A | 5/2000 | Saettone et al. |
| 6,123,068 A | 9/2000 | Lloyd et al. |
| 6,143,227 A | 11/2000 | Heiden et al. |
| 6,197,934 B1 | 3/2001 | DeVore et al. |
| 6,221,398 B1 | 4/2001 | Jakupovic et al. |
| 6,261,547 B1 | 7/2001 | Bawa et al. |
| 6,268,533 B1 | 7/2001 | Gao et al. |
| 6,313,176 B1 | 11/2001 | Ellinwood, Jr. |
| 6,378,519 B1 | 4/2002 | Davies et al. |
| 7,563,768 B2 | 7/2009 | Nakamura et al. |
| 7,568,480 B2 | 8/2009 | Foley et al. |
| 7,601,355 B2 | 10/2009 | Howard et al. |
| 7,638,549 B2 | 12/2009 | Coleman et al. |
| 9,211,269 B2 * | 12/2015 | Chen ............... A61K 31/05 |
| 2004/0087651 A1 | 5/2004 | Pereira Da Fonseca |
| 2008/0275057 A1 | 11/2008 | Kawabe et al. |
| 2009/0281522 A1 | 11/2009 | Thio et al. |
| 2009/0291894 A1 | 11/2009 | Tezapsidis |
| 2009/0317377 A1 | 12/2009 | Yeomans |
| 2009/0326275 A1 | 12/2009 | DiMauro |
| 2009/0328239 A1 | 12/2009 | Brauner et al. |
| 2010/0113780 A1 | 5/2010 | Kuroita et al. |
| 2010/0113819 A1 | 5/2010 | Belfadhel et al. |
| 2013/0203828 A1 | 8/2013 | Chen |
| 2013/0331422 A1 | 12/2013 | Chen et al. |
| 2014/0161762 A1 | 6/2014 | Patil et al. |

OTHER PUBLICATIONS

International Search Report dated Aug. 17, 2016 corresponding to International Search Report No. PCT/US2016/17543; 5 pages.
Written Opinion dated dated Aug. 17, 2016 corresponding to International Search Report No. PCT/US2016/17543; 5 pages.

* cited by examiner

Primary Examiner — Yevegeny Valenrod
(74) Attorney, Agent, or Firm — Leason Ellis LLP

(57) ABSTRACT

A pharmaceutical composition is provided which includes perillyl alcohol conjugated with a therapeutic agent and further includes and a hydrolyzable acylated aliphatic tail. A method of using the pharmaceutical composition is also provided for treating a condition or disease of a patient, e.g., cancer.

15 Claims, 5 Drawing Sheets
(5 of 5 Drawing Sheet(s) Filed in Color)

PHARMACEUTICAL COMPOSITIONS COMPRISING PERILLYL ALCOHOL DERIVATIVES

CROSS REFERENCE TO RELATED APPLICATIONS

This application claims priority to U.S. Provisional Patent Application Ser. No. 62/115,396, filed on Feb. 12, 2015 which is incorporated by reference in its entirety.

FIELD OF THE INVENTION

The present invention relates to monoterpene derivatives containing a therapeutic agent as well as an aliphatic tail. The present invention further relates to methods and compositions of using the monoterpene derivatives to treat cancer.

BACKGROUND

Malignant gliomas, the most common form of central nervous system (CNS) cancers, is currently considered essentially incurable. Among the various malignant gliomas, anaplastic astrocytomas (Grade III) and glioblastoma multiforme (GBM; Grade IV) have an especially poor prognosis due to their aggressive growth and resistance to currently available therapies. The present standard of care for malignant gliomas consists of surgery, ionizing radiation, and chemotherapy. Despite recent advances in medicine, the past 50 years have not seen any significant improvement in prognosis for malignant gliomas. Wen et al. Malignant gliomas in adults. *New England J Med.* 359: 492-507, 2008. Stupp et al. Radiotherapy plus concomitant and adjuvant temozolomide for glioblastoma. *New England J Med.* 352: 987-996, 2005.

The poor response of tumors, including malignant gliomas, to various types of chemotherapeutic agents are often due to intrinsic drug resistance. Additionally, acquired resistance of initially well-responding tumors and unwanted side effects are other problems that frequently thwart long-term treatment using chemotherapeutic agents. Hence, various analogues of chemotherapeutic agents have been prepared in an effort to overcome these problems. The analogues include novel therapeutic agents which are hybrid molecules of at least two existing therapeutic agents. For example, cisplatin has been conjugated with Pt-(II) complexes with cytotoxic codrugs, or conjugated with bioactive shuttle components such as porphyrins, bile acids, hormones, or modulators that expedite the transmembrane transport or the drug accumulation within the cell. (6-Aminomethylnicotinate) dichloridoplatinum(II) complexes esterified with terpene alcohols were tested on a panel of human tumor cell lines. The terpenyl moieties in these complexes appeared to fulfill a transmembrane shuttle function and increased the rate and extent of the uptake of these conjugates into various tumor cell lines. Schobert et al. Monoterpenes as Drug Shuttles: Cytotoxic (6-minomethylnicotinate) dichloridoplatinum(II) Complexes with Potential to Overcome Cisplatin Resistance. *J. Med. Chem.* 2007, 50, 1288-1293.

Perillyl alcohol (POH), a naturally occurring monoterpene, has been suggested to be an effective agent against a variety of cancers, including CNS cancer, breast cancer, pancreatic cancer, lung cancer, melanomas and colon cancer. Gould, M. Cancer chemoprevention and therapy by monoterpenes. *Environ Health Perspect.* 1997 June; 105 (Suppl 4): 977-979. Hybrid molecules containing both perillyl alcohol and retinoids were prepared to increase apoptosis-inducing activity. Das et al. Design and synthesis of potential new apoptosis agents: hybrid compounds containing perillyl alcohol and new constrained retinoids. *Tetrahedron Letters* 2010, 51, 1462-1466.

Co-owned U.S. Patent Publication No. 20130203828 disclosed various perillyl alcohol derivatives such as perillyl alcohol carbamates. For example, the perillyl alcohol derivatives include perillyl alcohol conjugated with a therapeutic agent such as dimethyl celocoxib (DMC), temozolomide (TMZ) or rolipram.

There is still a need for perillyl alcohol derivatives with improved properties for transdermal or topical application, as well as use the derivatives in the treatment of cancers such as malignant gliomas, skin cancers as well as precancerous skin conditions.

SUMMARY OF THE INVENTION

In one aspect of the present application, a pharmaceutical composition is provided. The composition comprises a compound comprising perillyl alcohol conjugated with a therapeutic agent, and an acylated aliphatic tail. The aliphatic tail can be derived from fatty acids. In some embodiments, the aliphatic tail contains 4 to 28 carbon atoms. The aliphatic chain can be saturated or unsaturated, branched or non-branched.

In one embodiment, the compound is a perillyl alcohol carbamate, where the nitrogen of the carbamate group is acylated with the aliphatic tail. In one embodiment, the therapeutic agent is a chemotherapeutic agent. The chemotherapeutic agent includes, but is not limited to, of a DNA alkylating agent, a topoisomerase inhibitor, an endoplasmic reticulum stress inducing agent, a platinum compound, an antimetabolite, an enzyme inhibitor, and a receptor antagonist. In specific embodiments, the therapeutic agent can be dimethyl celocoxib (DMC), temozolomide (TMZ), or rolipram.

In one embodiment, the compound is (3-Methyl-4-oxo-3,4-dihydro-imidazo[5,1-d][1,2,3,5]tetrazine-8-carbonyl)-octadeca-9,12-dienoyl-carbamic acid 4-isopropenyl-cyclohex-1-enylmethyl ester. In another embodiment, the compound is (3-Methyl-4-oxo-3,4-dihydro-imidazo[5,1-d][1,2,3,5]tetrazine-8-carbonyl)-hexadecanoic acid 4-isopropenyl-cyclohex-1-enylmethyl ester.

In another aspect, there is provided compounds of the Formula I;

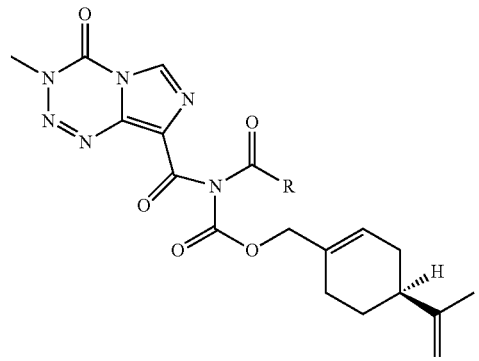

wherein R is selected from a $C_4$ to $C_{28}$ linear or branched alkyl, $C_4$ to $C_{28}$ alkeneyl or a $C_4$ to $C_{28}$ alkynyl group; or a pharmaceutically acceptable salt thereof.

In another aspect there is provided a compound according to Formula I wherein R is a $C_4$ to $C_{28}$ linear or branched alkeneyl containing 1, 2, 3, 4 or 5 double bonds.

In another aspect there is provided a compound according to Formula I wherein R is a $C_4$ to $C_{28}$ linear or branched alkynyl containing 1, 2, 3, 4 or 5 triple bonds.

In another aspect a compound of the Formula II;

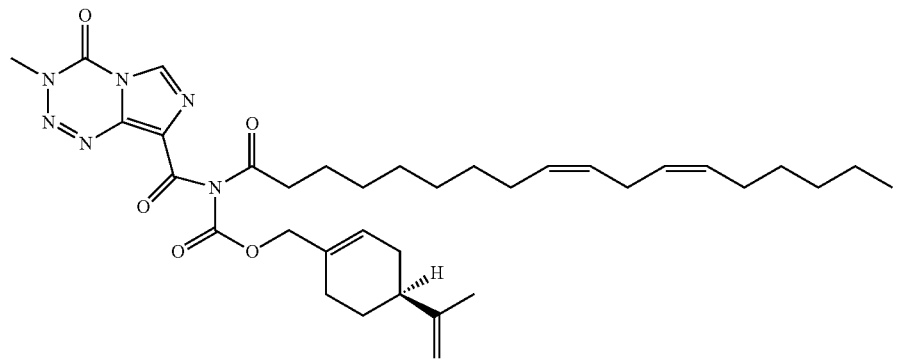 [SMILES: C=C(C)[C@@H]1CC=C(COC(=O)N(C(=O)CCCCCCC/C=C\C/C=C\CCCCC)C(=O)c2ncn3c(=O)n(C)nnc23)CC1]

or a pharmaceutically acceptable salt thereof is provided.
In another aspect, a compound of the Formula III is provided;

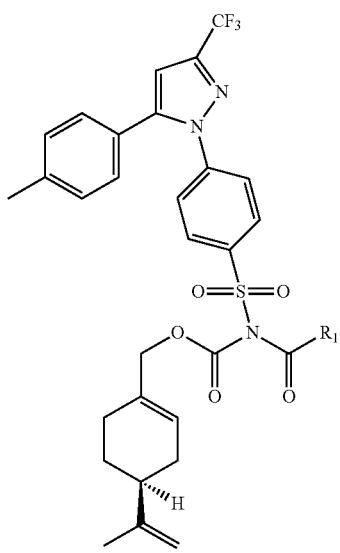

wherein $R_1$ is selected from a $C_4$ to $C_{28}$ linear or branched alkyl, linear or branched $C_4$ to $C_{28}$ alkeneyl or a linear or branched $C_4$ to $C_{28}$ alkynyl group; or a pharmaceutically acceptable salt thereof.

In another aspect there is provided a compound according to Formula III wherein $R_1$ is a $C_4$ to $C_{28}$ linear or branched alkeneyl containing 1, 2, 3, 4 or 5 double bonds.

In another aspect there is provided a compound according to Formula III wherein $R_1$ is a $C_4$ to $C_{28}$ linear or branched alkynyl containing 1, 2, 3, 4 or 5 triple bonds.

In another aspect a compound of the Formula IV; or a pharmaceutically acceptable salt thereof is provided.

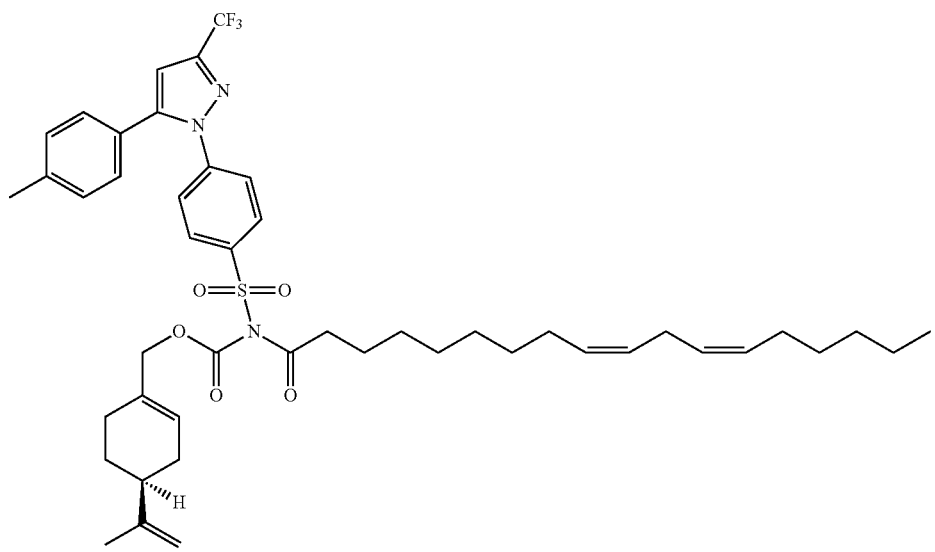 [SMILES: C=C(C)[C@@H]1CC=C(COC(=O)N(C(=O)CCCCCCC/C=C\C/C=C\CCCCC)S(=O)(=O)c2ccc(-n3nc(C(F)(F)F)cc3-c3ccc(C)cc3)cc2)CC1]

In another aspect, the present invention provides a method for treating a disease in a mammal. The method comprises delivering to the mammal a therapeutically effective amount of a pharmaceutical composition described herein. In one embodiment, the disease is cancer. For example, the cancer is a tumor of the nervous system, e.g., glioblastoma. The cancer can also be a skin cancer, such as melanoma, basal cell carcinoma, and squamous cell carcinoma. In another embodiment, the disease is a precancerous skin lesion. The composition can be administered by inhalation, intranasally, orally, intravenously, topically, transdermally, subcutaneously or intramuscularly.

In another aspect a process for making a compound of the Formula I

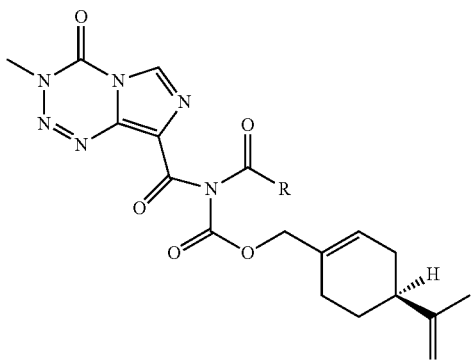

comprising the steps of a) reacting Temozolamide with oxalyl chloride in a halogenated solvent, preferably 1,2 dichloroethane, to give the isocyanate of Temozolamide Formula A

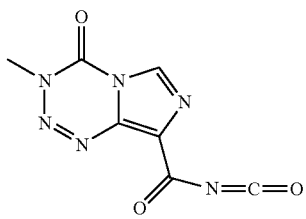 [SMILES: Cn1nnc2c(C(=O)N=C=O)ncn2c1=O]

b) reacting the isocyanate of Temozolamide with perillyl alcohol in a halogenated solvent to afford a compound of Formula B

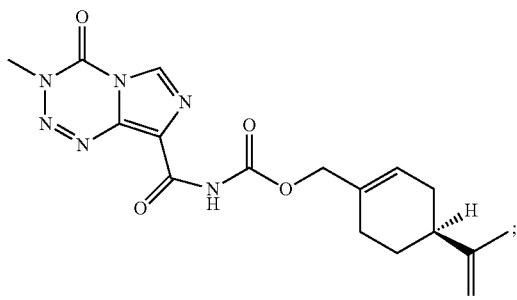 [SMILES: C=C(C)[C@@H]1CC=C(COC(=O)NC(=O)c2ncn3c(=O)n(C)nnc23)CC1]

c) reacting the compound of Formula B with an acid chloride, preferably linoleic acid chloride, of the Formula C

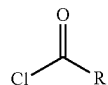

wherein R is selected from the group consisting of a $C_4$ to $C_{28}$ linear or branched alkyl, linear or branched $C_4$ to $C_{28}$ alkeneyl containing 1, 2, 3, 4, or 5 double bonds or a linear or branched $C_4$ to $C_{28}$ alkynyl group; containing 1, 2, 3, 4 or 5 triple bonds in the presence of a base, preferably NaH, in an ethereal solvent, preferably THF, to afford a compound of the Formula I is provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
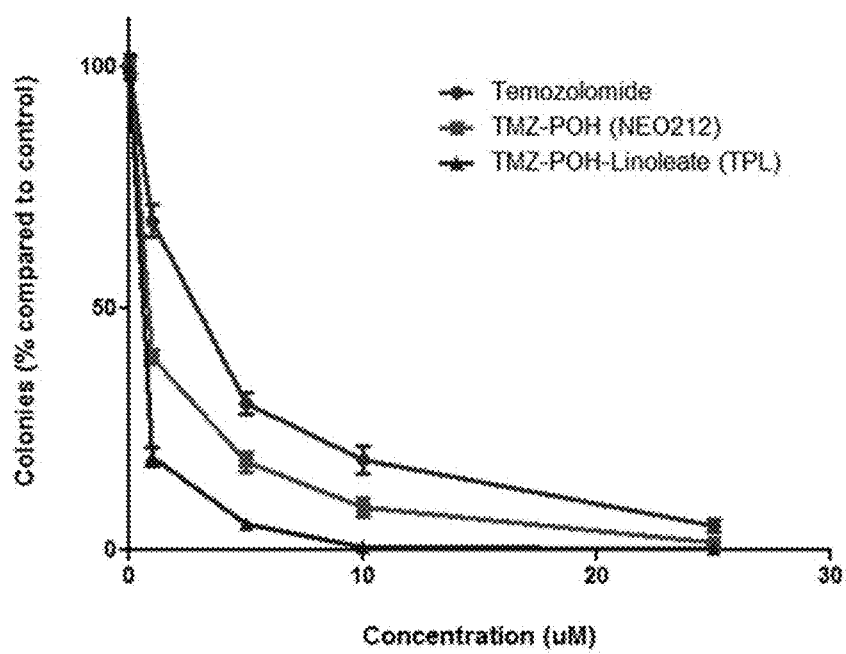
FIG. 1 is a plot showing in vitro efficacy of temozolomide (TMZ), TMZ-POH, and TMZ-POH-linoleate (TPL) in the treatment of MGMT negative human melanoma cells A2058.

In one aspect, the present invention provides for derivatives of monoterpene (or sesquiterpene) comprising a monoterpene (or sesquiterpene) conjugated with a therapeutic agent. The monoterpene (or sesquiterpene) derivative can further include an acylated aliphatic tail. In some embodiments, the aliphatic tail contains 4 to 28 carbon atoms. As an example, the monoterpene (or sesquiterpene) can be perillyl alcohol (POH). The therapeutic agent may be covalently linked with the monoterpene (or sesquiterpene) through carbamate, ester, ether bonds, or any other suitable chemical functional groups. For example, the monoterpene derivative can be perillyl alcohol carbamate of a therapeutic agent wherein the nitrogen of the carbamate group is acylated with the aliphatic tail. The therapeutic agent can be a chemotherapeutic agent, such as a DNA alkylating agent, a topoisomerase inhibitor, an endoplasmic reticulum stress inducing agent, a platinum compound, an antimetabolite, an enzyme inhibitor, or a receptor antagonist. In particular embodiments, the therapeutic agent can be dimethyl celocoxib (DMC), temozolomide (TMZ), or rolipram. The molar ratio of the monoterpene (or sesquiterpene) to the therapeutic agent in the monoterpene (or sesquiterpene) conjugate may be 1:1, 1:2, 1:3, 1:4, 2:1, 3:1, 4:1, or any other suitable molar ratios. When the monoterpene (or sesquiterpene) and the therapeutic agent are conjugated through a carbamate bond, the therapeutic agent may be any agent bearing at least one carboxylic acid functional group, or any agent bearing at least one amine functional group. The aliphatic chain can be saturated or unsaturated, straight chain or branched-chain.

As used herein, monoterpenes include terpenes that consist of two isoprene units. Monoterpenes may be linear (acyclic) or contain rings. Derivatives of monoterpenoids are also encompassed by the present invention. Monoterpenoids may be produced by biochemical modifications such as oxidation or rearrangement of monoterpenes. Examples of monoterpenes and monoterpenoids include, perillyl alcohol (S(−)) and (R(+)), ocimene, myrcene, geraniol, citral, citronellol, citronellal, linalool, pinene, terpineol, terpinen, limonene, terpinenes, phellandrenes, terpinolene, terpinen-4-ol (or tea tree oil), pinene, terpineol, terpinen; the terpenoids such as p-cymene which is derived from monocyclic terpenes such as menthol, thymol and carvacrol; bicyclic monoterpenoids such as camphor, borneol and eucalyptol.

Monoterpenes may be distinguished by the structure of a carbon skeleton and may be grouped into acyclic monoterpenes (e.g., myrcene, (Z)- and (E)-ocimene, linalool, geraniol, nerol, citronellol, myrcenol, geranial, citral a, neral, citral b, citronellal, etc.), monocyclic monoterpenes (e.g., limonene, terpinene, phellandrene, terpinolene, menthol, carveol, etc.), bicyclic monoterpenes (e.g., pinene, myrtenol, myrtenal, verbanol, verbanon, pinocarveol, carene, sabinene, camphene, thujene, etc.) and tricyclic monoterpenes (e.g. tricyclene). See *Encyclopedia of Chemical Technology*, Fourth Edition, Volume 23, page 834-835.

Sesquiterpenes of the present invention include terpenes that consist of three isoprene units. Sesquiterpenes may be linear (acyclic) or contain rings. Derivatives of sesquiterpenoids are also encompassed by the present invention. Sesquiterpenoids may be produced by biochemical modifications such as oxidation or rearrangement of sesquiterpenes. Examples of sesquiterpenes include farnesol, farnesal, farnesylic acid and nerolidol.

The derivatives of monoterpene (or sesquiterpene) include, but are not limited to, carbamates, esters, ethers, alcohols and aldehydes of the monoterpene (or sesquiterpene). Monoterpene (or sesquiterpene) alcohols may be derivatized to carbamates, esters, ethers, aldehydes or acids.

Carbamate refers to a class of chemical compounds sharing the functional group

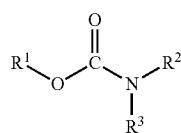

based on a carbonyl group flanked by an oxygen and a nitrogen. The R groups on the nitrogen and the oxygen may form a ring. $R^1$—OH may be a monoterpene, e.g., POH. In some embodiments, one of $R^2$ and $R^3$ may be a therapeutic agent, while the other of $R^2$ and $R^3$ is an acylated aliphatic chain having 4-28 carbons.

Carbamates may be synthesized by reacting isocyanate and alcohol, or by reacting chloroformate with amine. Carbamates may be synthesized by reactions making use of phosgene or phosgene equivalents. For example, carbamates may be synthesized by reacting phosgene gas, diphosgene or a solid phosgene precursor such as triphosgene with two amines or an amine and an alcohol. Carbamates (also known as urethanes) can also be made from reaction of a urea intermediate with an alcohol. Dimethyl carbonate and diphenyl carbonate are also used for making carbamates. Alternatively, carbamates may be synthesized through the reaction of alcohol and/or amine precursors with an ester-substituted diaryl carbonate, such as bismethylsalicylcarbonate (BMSC). U.S. Patent Publication No. 20100113819.

Carbamates may be synthesized by the following approach:

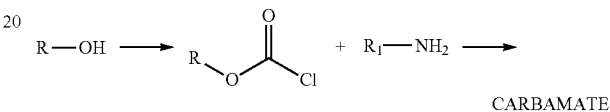

Monoterpenes or sesquiterpines (e.g POH) are reacted with phosgene in the presence of a first base such and an aromatic solvent such as toluene to form the corresponding chloroformate. The chloroformates are then reacted with a therapeutic agent having an $NH_2$ group (e.g DMC) optionally in the presence of a second base to afford the carbamate. The carbamates can then be reacted with an acid chloride of a $C_4$ to $C_{28}$ linear or branched alkyl carboxylic acid, a $C_4$ to $C_{28}$ alkeneyl carboxylic acid having 1-5 double bonds or a $C_4$ to $C_{28}$ alkynyl carboxylic acid having 1-5 triple bonds; optionally in the presence of a third base. Suitable reaction solvents include, but are not limited to, tetrahydrofuran, dichloromethane, dichloroethane, acetone, and diisopropyl ether. The reaction may be performed at a temperature ranging from about −70° C. to about 80° C., or from about −65° C. to about 50° C. The molar ratio of perillyl chloroformate (or the chloroformate of a monoterpene or sesquiterpene) to the substrate $R_1$—$NH_2$ (wherein $R_1$—$NH_2$ is a therapeutic agent) may range from about 1:1 to about 2:1, from about 1:1 to about 1.5:1, from about 2:1 to about 1:1, or from about 1.05:1 to about 1.1:1. Suitable first, second and third bases include, but are not limited to, organic bases, such as triethylamine, N,N'-diisopropylethylamine, butyl lithium, and potassium-t-butoxide and inorganic bases such as sodium or potassium carbonate, KOH, NaOH and NaH.

Alternatively, carbamates may be synthesized by the following approach:

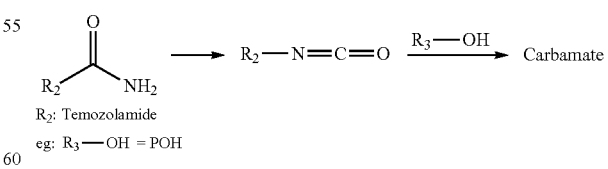

$R_2$: Temozolamide eg: $R_3$—OH = POH $R_2C(O)NH_2$ (where $R_2C(O)NH_2$ is a therapeutic agent e.g TMZ) is reacted with oxalyl chloride to produce the isocyanate ($R_2$—N=C=O) followed by reaction with a monoterpene or sesquiterpene (e.g POH) to afford the carbamate, optionally in the presence of a first base. The carbamates can then be reacted with an acid chloride of a $C_4$ to $C_{28}$ linear or branched alkyl carboxylic acid, a $C_4$ to $C_{28}$ alkeneyl carboxylic acid having 1-5 double bonds or a $C_4$ to $C_{28}$ alkynyl carboxylic acid having 1-5 triple bonds; optionally in the presence of a second base. Suitable reaction solvents include, but are not limited to, dichloromethane, dichloroethane, toluene, diisopropyl ether, and tetrahydrofuran. The reaction may be performed at a temperature ranging from about 25° C. to about 110° C., or from about 30° C. to about 80° C., or about 50° C. The molar ratio of perillyl alcohol (or monoterpene or sesquiterpene) to the substrate $R_2$—N=C=O may range from about 1:1 to about 2:1, from about 1:1 to about 1.5:1, from about 2:1 to about 1:1, or from about 1.05:1 to about 1.1:1. Suitable first, second and third bases include, but are not limited to, organic bases, such as triethylamine, N,N'-diisopropylethylamine, butyl lithium, and potassium-t-butoxide or inorganic bases such as but not limited to potassium or sodium carbonate, NaOH, KOH, and NaH.

Esters of the monoterpene (or sesquiterpene) alcohols of the present invention can be derived from an inorganic acid or an organic acid. Inorganic acids include, but are not limited to, phosphoric acid, sulfuric acid, and nitric acid. Organic acids include, but are not limited to, carboxylic acid such as benzoic acid, fatty acid, acetic acid and propionic acid, and any therapeutic agent bearing at least one carboxylic acid functional group Examples of esters of monoterpene (or sesquiterpene) alcohols include, but are not limited to, carboxylic acid esters (such as benzoate esters, fatty acid esters (e.g., palmitate ester, linoleate ester, stearate ester, butyryl ester and oleate ester), acetates, propionates (or propanoates), and formates), phosphates, sulfates, and carbamates (e.g., N,N-dimethylaminocarbonyl).

A specific example of a monoterpene that may be used in the present invention is perillyl alcohol. The derivatives of perillyl alcohol include perillyl alcohol carbamates, perillyl alcohol esters, perillic aldehydes, dihydroperillic acid, perillic acid, perillic aldehyde derivatives, dihydroperillic acid esters and perillic acid esters.

In certain embodiments, a POH carbamate is synthesized by a process comprising the step of reacting a first reactant of perillyl chloroformate with a second reactant such as dimethyl celocoxib (DMC), temozolomide (TMZ) and rolipram. The reaction may be carried out in the presence of tetrahydrofuran and a base such as n-butyl lithium. Perillyl chloroformate may be made by reacting POH with phosgene. For example, POH conjugated with temozolomide through a carbamate bond may be synthesized by reacting temozolomide with oxalyl chloride followed by reaction with perillyl alcohol. The reaction may be carried out in the presence of 1,2-dichloroethane.

As described herein, the monoterpene derivative, such as POH carbamate conjugated with another therapeutic agent, can be further reacted with a fatty acid to form a tri-conjugate structure containing an acylated aliphatic tail (which is the fatty acid with the terminal —OH of the carboxyl group removed). The fatty acid can be unsaturated, such as Caprylic acid, Capric acid, Lauric acid, Myristic acid, Palmitic acid, Stearic acid, Arachidic acid, Behenic acid, Lignoceric acid, Cerotic acid; or saturated, such as Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid. For example, when the therapeutic agent is TMZ, the fatty acid can be linoleic acid to form (3-Methyl-4-oxo-3,4-dihydro-imidazo[5,1-d][1,2,3,5]tetrazine-8-carbonyl)-octadeca-9,12-dienoyl-carbamic acid 4-isopropyl-cyclohex-1-enylmethyl ester, or it can be palmitic acid to form (3-Methyl-4-oxo-3,4-dihydro-imidazo[5,1-d][1,2,3,5]tetrazine-8-carbonyl)-hexadecanoic acid 4-isopropyl-cyclohex-1-enylmethyl ester. Halides of the fatty acid (e.g., acyl bromide, acyl chloride of these fatty acids), or anhydrides of the fatty acid can also be used. For example, a POH carbamate that is a conjugate with a therapeutic agent can be further reacted with a fatty acid (or a fatty acid halide or anhydride) such that the hydrogen of the —NH— group in the carbamate linker group is substituted with the acylated aliphatic tail of the fatty acid.

Except where stated otherwise, the following definitions apply throughout the present specification and claims. These definitions apply regardless of whether a term is used by itself or in combination with other terms. For example, the definition of "alkyl" applies not only to alkyl groups per se, but also to the alkyl portions of alkoxy, alkylamino, alkylthio or alkylcarbonyl groups etc. Furthermore all ranges described for a chemical group, for example "from 1 to 13 carbon atoms" or "$C_1$-$C_6$ alkyl" include all combinations and sub-combinations of ranges and specific numbers of carbon atoms therein.

As described herein, "Alkyl" means a straight (linear) chain or branched chain aliphatic hydrocarbon group having from 4 to 28 carbon atoms in the chain. Preferred alkyl groups have from 10 to 20 carbon atoms in the chain. More preferred alkyl groups have from 14 to 20 carbon atoms in the chain. Non limiting examples of suitable alkyl groups include isopropyl, sec-butyl, n-butyl, and t-butyl.

As described herein "Alkenyl" means a straight (linear) chain or branched chain aliphatic hydrocarbon group having 1 to 8, preferably 1 to 5, more preferably 1 to 3, carbon-carbon double bonds and having from 4 to 28 carbon atoms in the chain. Preferred alkenyl groups have from 10 to 20 carbon atoms in the chain. More preferred alkenyl groups have from 14 to 20 carbon atoms in the chain. Non limiting examples of suitable alkenyl groups include isopropenyl, n-butenyl, 1-hexenyl and 3-methylbut-2-enyl.

As described herein "Alkynyl" means a straight (linear) chain or branched chain aliphatic hydrocarbon group having at 1 to 5 carbon-carbon triple bonds and having from 4 to 28 carbon atoms in the chain. Preferred alkynyl groups have from 4 to 12 carbon atoms in the chain. More preferred alkynyl groups have from 4 to 6 carbon atoms in the chain. Examples of suitable 2-propynyl and 2-butynyl.

According to the present invention, the therapeutic agents that may be conjugated with monoterpene (or sesquiterpene) include, but are not limited to, chemotherapeutic agents, therapeutic agents for treatment of CNS disorders (including, without limitation, primary degenerative neurological disorders such as Alzheimer's, Parkinson's, multiple sclerosis, Attention-Deficit Hyperactivity Disorder or ADHD, psychological disorders, psychosis and depression), immunotherapeutic agents, angiogenesis inhibitors, and anti-hypertensive agents. Anti-cancer agents that may be conjugated with monoterpene or sesquiterpene can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; or disappearance of markers associated with undesirable, unwanted, or aberrant cell proliferation. U.S. Patent Publication No. 20080275057.

Also encompassed by the present invention is admixtures and/or coformulations of a monoterpene (or sesquiterpene) and at least one therapeutic agent.

Chemotherapeutic agents include, but are not limited to, DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, tyrosine kinase inhibitors, boron radiosensitizers (i.e. velcade), and chemotherapeutic combination therapies.

Non-limiting examples of DNA alkylating agents are nitrogen mustards, such as Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, Triaziquone, Triethylenemelamine; Hydrazines (Procarbazine); Triazenes such as Dacarbazine and Temozolomide (TMZ); Altretamine and Mitobronitol.

Non-limiting examples of Topoisomerase I inhibitors include Campothecin derivatives including SN-38, APC, NPC, campothecin, topotecan, exatecan mesylate, 9-nitro-camptothecin, 9-aminocamptothecin, lurtotecan, rubitecan, silatecan, gimatecan, diflomotecan, extatecan, BN-80927, DX-8951f, and MAG-CPT as described in Pommier Y. (2006) Nat. Rev. Cancer 6(10):789-802 and U.S. Patent Publication No. 200510250854; Protoberberine alkaloids and derivatives thereof including berberrubine and coralyne as described in Li et al. (2000) Biochemistry 39(24):7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11 (8): 1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-]25, Crow et al. (1994) J. Med. Chem. 37(19):31913194, and Crespi et al. (1986) Biochem. Biophys. Res. Commun. 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-I03 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e]pyrimidines, and Anthracenyl-amino Acid Conjugates as described in Denny and Baguley (2003) Curr. Top. Med. Chem. 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Platinum based compounds are a subclass of DNA alkylating agents. Non-limiting examples of such agents include Cisplatin, Nedaplatin, Oxaliplatin, Triplatin tetranitrate, Satraplatin, Aroplatin, Lobaplatin, and JM-216. (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"FOLFOX" is an abbreviation for a type of combination therapy that is used to treat colorectal cancer. It includes 5-FU, oxaliplatin and leucovorin. Information regarding this treatment is available on the National Cancer Institute's web site, cancer.gov, last accessed on Jan. 16, 2008.

"FOLFOX/BV" is an abbreviation for a type of combination therapy that is used to treat colorectal cancer. This therapy includes 5-FU, oxaliplatin, leucovorin and Bevacizumab. Furthermore, "XELOX/BV" is another combination therapy used to treat colorectal cancer, which includes the prodrug to 5-FU, known as Capecitabine (Xeloda) in combination with oxaliplatin and bevacizumab. Information regarding these treatments are available on the National Cancer Institute's web site, cancer.gov or from 23 the National Comprehensive Cancer Network's web site, nccn.org, last accessed on May 27, 2008.

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-I (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifarnib); CDK inhibitor (Alvocidib, Seliciclib); proteasome inhibitor (Bortezomib); phosphodiesterase inhibitor (Anagrelide; rolipram); IMP dehydrogenase inhibitor (Tiazofurine); and lipoxygenase inhibitor (Masoprocol). Examples of receptor antagonists include, but are not limited to ERA (Atrasentan); retinoid X receptor (Bexarotene); and a sex steroid (Testolactone).

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-ab1 (Imatinib, Nilotinib, Dasatinib); Src (Bosutinib) and Janus kinase 2 (Lestaurtinib).

"Lapatinib" (Tykerb®) is an dual EGFR and erbB-2 inhibitor. Lapatinib has been investigated as an anticancer monotherapy, as well as in combination with trastuzumab, capecitabine, letrozole, paclitaxel and FOLFIRI (irinotecan, 5-fluorouracil and leucovorin), in a number of clinical trials. It is currently in phase III testing for the oral treatment of metastatic breast, head and neck, lung, gastric, renal and bladder cancer.

A chemical equivalent of lapatinib is a small molecule or compound that is a tyrosine kinase inhibitor (TKI) or alternatively a HER-1 inhibitor or a HER-2 inhibitor. Several TKIs have been found to have effective antitumor activity and have been approved or are in clinical trials. Examples of such include, but are not limited to, Zactima (ZD6474), Iressa (gefitinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (*SUI* 1248) and lefltmomide (SU101).

PTK/ZK is a tyrosine kinase inhibitor with broad specificity that targets all VEGF receptors (VEGFR), the platelet-derived growth factor (PDGF) receptor, c-KIT and c-Fms. Drevs (2003) Idrugs 6(8):787-794. PTK/ZK is a targeted drug that blocks angiogenesis and lymphangiogenesis by inhibiting the activity of all known receptors that bind VEGF including VEGFR-I (Flt-1), VEGFR-2 (KDR/Flk-1) and VEGFR-3 (Flt-4). The chemical names of PTK/ZK are 1-[4-Chloroanilino]-4-[4-pyridylmethyl]phthalazine Succinate or 1-Phthalazinamine, N-(4-chlorophenyl)-4-(4-pyridinylmethyl)-butanedioate (1:1). Synonyms and analogs of PTK/TK are known as Vatalanib, CGP79787D, PTK787/ZK 222584, CGP-79787, DE-00268, PTK-787, PTK787A, VEGFR-TK inhibitor, ZK 222584 and ZK.

Chemotherapeutic agents that can be conjugated with monoterpene or sesquiterpene may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

The monoterpene or sesquiterpene derivative may be conjugated with angiogenesis inhibitors. Examples of angiogenesis inhibitors include, but are not limited to, angiostatin, angiozyme, antithrombin III, AG3340, VEGF inhibitors, batimastat, bevacizumab (avastin), BMS-275291, CAI, 2C3, HuMV833 Canstatin, Captopril, carboxyamidotriazole, cartilage derived inhibitor (CDI), CC-5013, 6-O-(chloroacetyl-carbonyl)-fumagillol, COL-3, combretastatin, combretastatin A4 Phosphate, Dalteparin, EMD 121974 (Cilengitide), endostatin, erlotinib, gefitinib (Iressa), genistein, halofuginone hydrobromide, Idl, Id3, IM862, imatinib mesylate, IMC-IC11 Inducible protein 10, interferon-alpha, interleukin 12, lavendustin A, LY317615 or AE-941, marimastat, mspin, medroxpregesterone acetate, Meth-1, Meth-2, 2-methoxyestradiol (2-ME), neovastat, oteopontin cleaved product, PEX, pigment epithelium growth factor (PEGF), platelet factor 4, prolactin fragment, proliferin-related protein (PRP), PTK787/ZK 222584, ZD6474, recombinant human platelet factor 4 (rPF4), restin, squalamine, SU5416, SU6668, SU11248 suramin, Taxol, Tecogalan, thalidomide, thrombospondin, TNP-470, troponin-1, vasostatin, VEG1, VEGF-Trap, and ZD6474.

Non-limiting examples of angiogenesis inhibitors also include, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, pentosan polysulfate, angiotensin II antagonists, cyclooxygenase inhibitors (including non-steroidal anti-inflammatory drugs (NSAIDs) such as aspirin and ibuprofen, as well as selective cyclooxygenase-2 inhibitors such as celecoxib and rofecoxib), and steroidal anti-inflammatories (such as corticosteroids, mineralocorticoids, dexamethasone, prednisone, prednisolone, methylpred, betamethasone).

Other therapeutic agents that modulate or inhibit angiogenesis and may also be conjugated with monoterpene or sesquiterpene include agents that modulate or inhibit the coagulation and fibrinolysis systems, including, but not limited to, heparin, low molecular weight heparins and carboxypeptidase U inhibitors (also known as inhibitors of active thrombin activatable fibrinolysis inhibitor [TAFIa]). U.S. Patent Publication No. 20090328239. U.S. Pat. No. 7,638,549.

Non-limiting examples of the anti-hypertensive agents include angiotensin converting enzyme inhibitors (e.g., captopril, enalapril, delapril etc.), angiotensin II antagonists (e.g., candesartan cilexetil, candesartan, losartan (or Cozaar), losartan potassium, eprosartan, valsartan (or Diovan), termisartan, irbesartan, tasosartan, olmesartan, olmesartan medoxomil etc.), calcium antagonists (e.g., manidipine, nifedipine, amlodipine (or Amlodin), efonidipine, nicardipine etc.), diuretics, renin inhibitor (e.g., aliskiren etc.), aldosterone antagonists (e.g., spironolactone, eplerenone etc.), beta-blockers (e.g., metoprolol (or Toporol), atenolol, propranolol, carvedilol, pindolol etc.), vasodilators (e.g., nitrate, soluble guanylate cyclase stimulator or activator, prostacycline etc.), angiotensin vaccine, clonidine and the like. U.S. Patent Publication No. 20100113780.

Other therapeutic agents that may be conjugated with monoterpene (or sesquiterpene) include, but are not limited to, Sertraline (Zoloft), Topiramate (Topamax), Duloxetine (Cymbalta), Sumatriptan (Imitrex), Pregabalin (Lyrica), Lamotrigine (Lamictal), Valaciclovir (Valtrex), Tamsulosin (Flomax), Zidovudine (Combivir), Lamivudine (Combivir), Efavirenz (Sustiva), Abacavir (Epzicom), Lopinavir (Kaletra), Pioglitazone (Actos), Desloratidine (Clarinex), Cetirizine (Zyrtec), Pentoprazole (Protonix), Lansoprazole (Prevacid), Rebeprazole (Aciphex), Moxifloxacin (Avelox), Meloxicam (Mobic), Dorzolamide (Truspot), Diclofenac (Voltaren), Enlapril (Vasotec), Montelukast (Singulair), Sildenafil (Viagra), Carvedilol (Coreg), Ramipril (Delix).

Table 1 lists pharmaceutical agents that can be conjugated with monoterpene (or sesquiterpene), including structure of the pharmaceutical agent and the preferred derivative for conjugation.

TABLE 1

| Brand Name | Generic Name | Activity | Structure | Preferred Derivative |
|---|---|---|---|---|
| Zoloft | Sertraline | Depression | 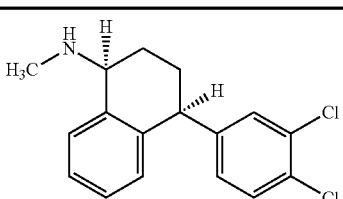 | Carbamate |
| Topamax | Topiramate | Seizures | 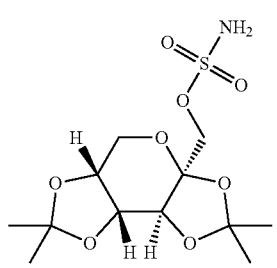 | Carbamate |
| Cymbalta | Duloxetine | Depression | 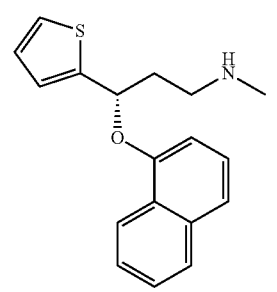 [SMILES: CNCC[C@H](Oc1cccc2ccccc12)c1cccs1] | Carbamate |
| Imitrex | Sumatriptan | Migraine | 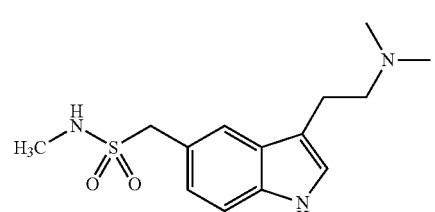 | Carbamate |
| Lyrica | Pregabalin | Neuropathic pain | 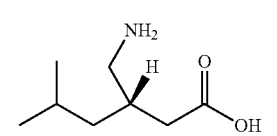 | Carbamate or Ester |
| Lamictal | Lamotrigine | Seizures | 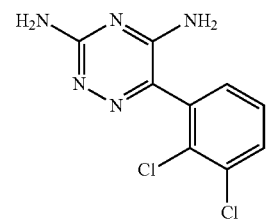 [SMILES: Nc1nnc(-c2cccc(Cl)c2Cl)c(N)n1] | Carbamate |
| Valtrex | Valaciclovir | Herpes | 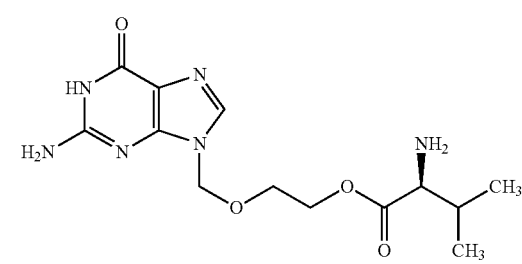 [SMILES: CC(C)[C@H](N)C(=O)OCCOCn1cnc2c(=O)[nH]c(N)nc21] | Carbamate |

TABLE 1-continued

| Brand Name | Generic Name | Activity | Structure | Preferred Derivative |
|---|---|---|---|---|
| Tarceva | Erlotinib | Non-small cell lung cancer | 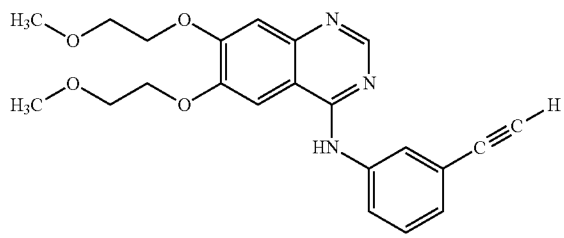 [SMILES: C#Cc1cccc(Nc2ncnc3cc(OCCOC)c(OCCOC)cc23)c1] | Carbamate |
| Flomax | Tamsulosin | Benign prostatic Cancer | 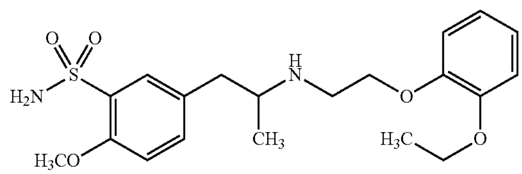 [SMILES: CCOc1ccccc1OCCNC(C)Cc1ccc(OC)c(S(N)(=O)=O)c1] | Carbamate |
| Gleevec | Imatinib | Leukemia | 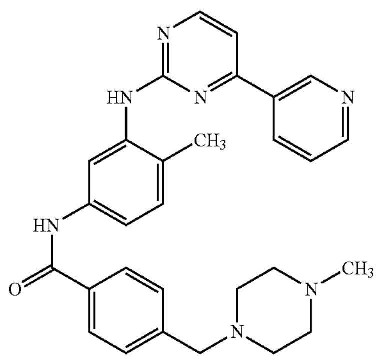 [SMILES: Cc1ccc(NC(=O)c2ccc(CN3CCN(C)CC3)cc2)cc1Nc1nccc(-c2cccnc2)n1] | Carbamate |
| Combivir | Zidovudine | HIV infection | | Carbamate |
| Combivir | Lamivudine | HIV infection | | Carbonate |

TABLE 1-continued

| Brand Name | Generic Name | Activity | Structure | Preferred Derivative |
|---|---|---|---|---|
| Sustiva | Efavirenz | HIV infection | 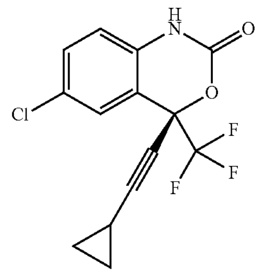 | Carbamate |
| Epzicom | Abacavir | HIV infection | 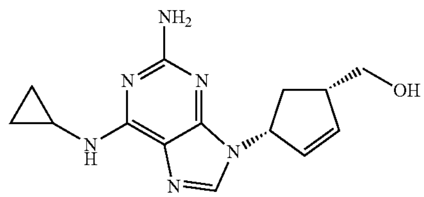 | Carbamate |
| Kaletra | Lopinavir | HIV infection | 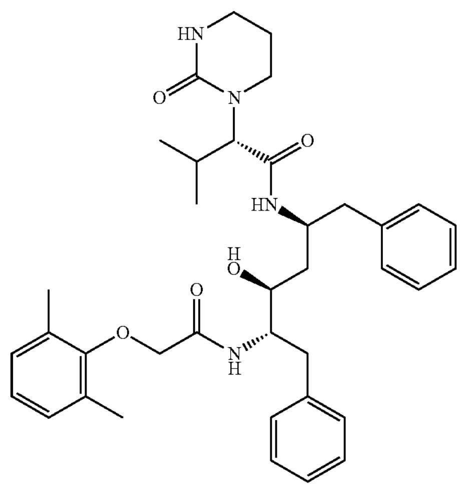 [SMILES: Cc1cccc(C)c1OCC(=O)N[C@@H](Cc1ccccc1)[C@@H](O)C[C@H](Cc1ccccc1)NC(=O)[C@H](C(C)C)N1CCCNC1=O] | Carbamate |
| Actos | Pioglitazone | Type-2 diabetes | 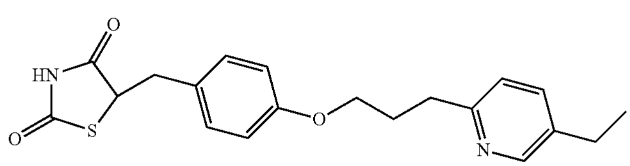 [SMILES: CCc1ccc(CCCOc2ccc(CC3SC(=O)NC3=O)cc2)nc1] | Carbamate |
| Clarinex | Desloratidine | Allergic rhinitis | 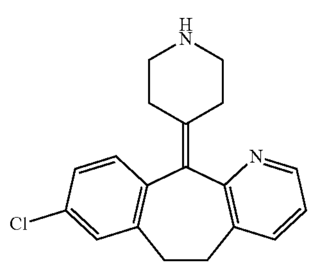 [SMILES: Clc1ccc2c(c1)CCc1cccnc1C2=C1CCNCC1] | Carbamate |

TABLE 1-continued

| Brand Name | Generic Name | Activity | Structure | Preferred Derivative |
|---|---|---|---|---|
| Zyrtec | Cetirizine | Allergic | 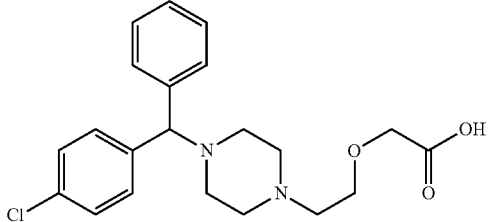 [SMILES: O=C(O)COCCN1CCN(C(c2ccccc2)c2ccc(Cl)cc2)CC1] | Ester |
| Protonix | Pentoprazole | Gastrointestinal | 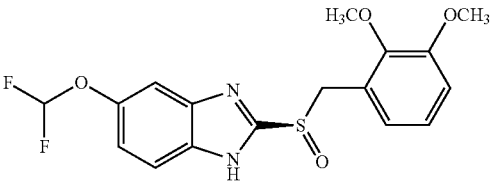 [SMILES: COc1cccc(C[S@@](=O)c2nc3cc(OC(F)F)ccc3[nH]2)c1OC] | Carbamate |
| Prevacid | Lansoprazole | Gastrointestinal | 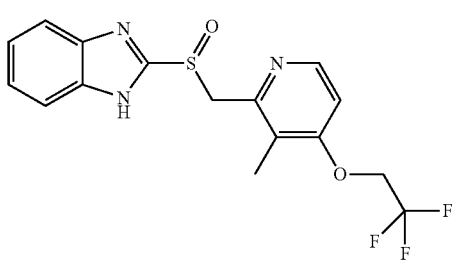 [SMILES: Cc1c(OCC(F)(F)F)ccnc1CS(=O)c1nc2ccccc2[nH]1] | Carbamate |
| Aciphex | Rebeprazole | Gastrointestinal | 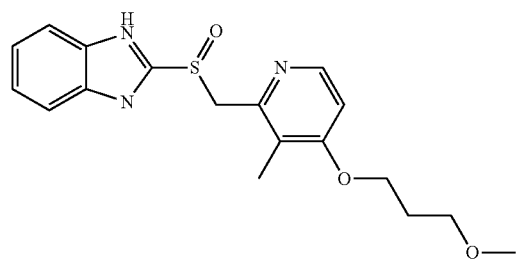 | Carbamate |
| Diovan | Valsartan | Hypertension | 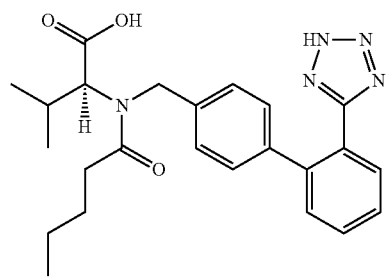 [SMILES: CCCCC(=O)N(Cc1ccc(-c2ccccc2-c2nn[nH]n2)cc1)[C@H](C(=O)O)C(C)C] | Carbamate |
| Cozaar | Losartan | Hypertension | 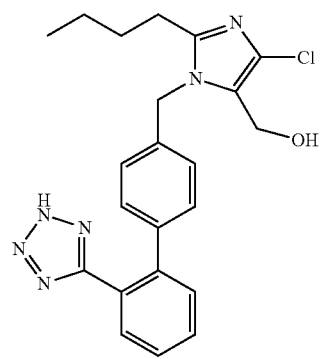 [SMILES: CCCCc1nc(Cl)c(CO)n1Cc1ccc(-c2ccccc2-c2nn[nH]n2)cc1] | Carbamate |

TABLE 1-continued

| Brand Name | Generic Name | Activity | Structure | Preferred Derivative |
|---|---|---|---|---|
| Avelox | Moxifloxacin | Bacterial infection | 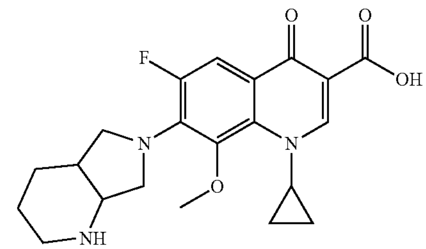 [SMILES: COc1c(N2CC3CCCNC3C2)c(F)cc2c(=O)c(C(=O)O)cn(C3CC3)c12] | Carbamate or Ester |
| Mobic | Meloxicam | Osteoarthritis | 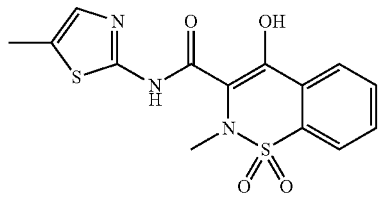 | Carbamate |
| Truspot | Dorzolamide | Intraocular pressure | 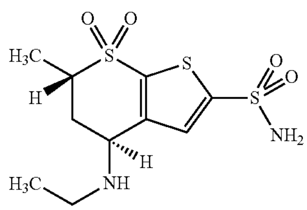 | Carbamate |
| Voltaren | Diclofenac | Osteoarthritis & rheumatoid arthritis | 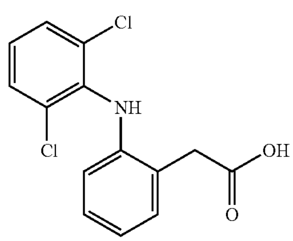 [SMILES: O=C(O)Cc1ccccc1Nc1c(Cl)cccc1Cl] | Carbamate or Ester |
| Vasotec | Enlapril | Hypertension | 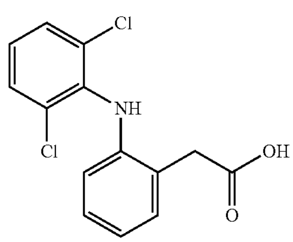 [SMILES: O=C(O)Cc1ccccc1Nc1c(Cl)cccc1Cl] | Carbamate or Ester |
| Singulair | Montelukast | Asthma | 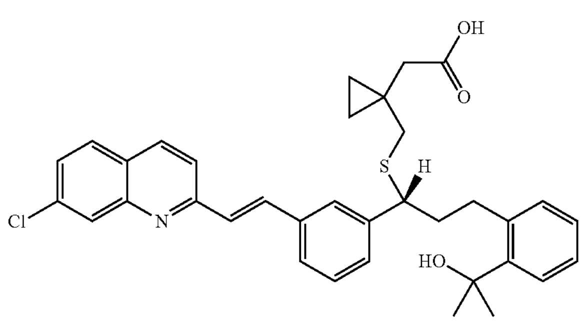 [SMILES: CC(C)(O)c1ccccc1CC[C@@H](SCC1(CC(=O)O)CC1)c1cccc(/C=C/c2ccc3ccc(Cl)cc3n2)c1] | Ester |

TABLE 1-continued

| Brand Name | Generic Name | Activity | Structure | Preferred Derivative |
|---|---|---|---|---|
| Amlodin | Amlodipine | Hypertension | 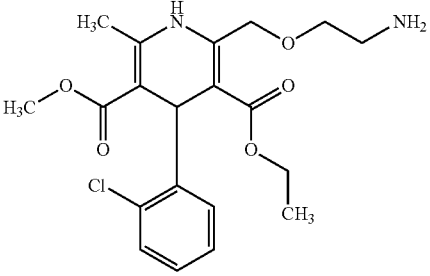 [SMILES: CCOC(=O)C1=C(COCCN)NC(C)=C(C(=O)OC)C1c1ccccc1Cl] | Carbamate |
| Toporol | Metoprolol | Hypertension | 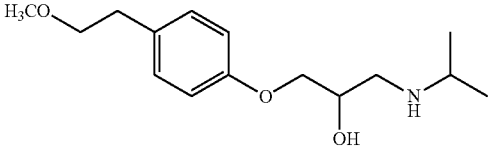 [SMILES: COCCc1ccc(OCC(O)CNC(C)C)cc1] | Carbamate |
| Viagra | Sildenafil | Erectile dysfunction | 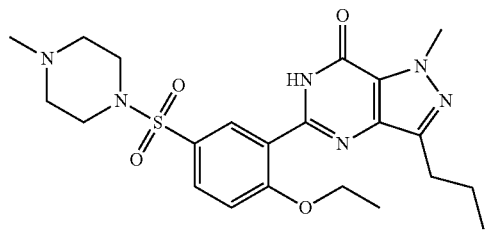 [SMILES: CCCc1nn(C)c2c(=O)[nH]c(-c3cc(S(=O)(=O)N4CCN(C)CC4)ccc3OCC)nc12] | Carbamate |
| Coreg | Carvedilol | Hypertension | 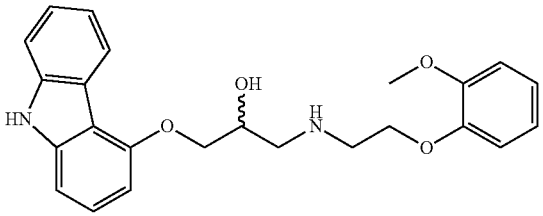 [SMILES: COc1ccccc1OCCNCC(O)COc1cccc2[nH]c3ccccc3c12] | Carbamate |
| Delix | Ramipril | Hypertension | 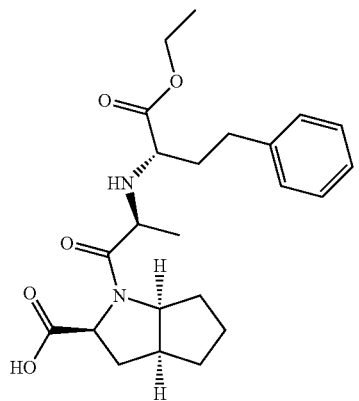 | Carbamate or Ester |
| Sinemet (Parcopa, Atamet) | L-DOPA | Neurological disorders | 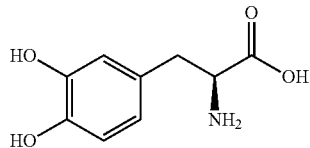 | |

The purity of the monoterpene (or sesquiterpene) derivatives may be assayed by gas chromatography (GC) or high pressure liquid chromatography (HPLC). Other techniques for assaying the purity of monoterpene (or sesquiterpene) derivatives and for determining the presence of impurities include, but are not limited to, nuclear magnetic resonance (NMR) spectroscopy, mass spectrometry (MS), GC-MS, infrared spectroscopy (IR), and thin layer chromatography (TLC). Chiral purity can be assessed by chiral GC or measurement of optical rotation.

The monoterpene (or sesquiterpene) derivatives may be purified by methods such as crystallization, or by separating the monoterpene (or sesquiterpene) derivative from impurities according to the unique physicochemical properties (e.g., solubility or polarity) of the derivative. Accordingly, the monoterpene (or sesquiterpene) derivative can be separated from the monoterpene (or sesquiterpene) by suitable separation techniques known in the art, such as preparative chromatography, (fractional) distillation, or (fractional) crystallization.

The invention also provides for methods of using the herein described monoterpenes (or sesquiterpenes) derivatives to treat a disease, such as cancer or other nervous system disorders. For example, the cancer is a tumor of the nervous system, e.g., glioblastoma. The cancer can also be a skin cancer, such as melanoma, basal cell carcinoma, or squamous cell carcinoma. The disease can also be a precancerous skin lesion.

A monoterpenes (or sesquiterpenes) derivative may be administered alone, or in combination with radiation, surgery or additional chemotherapeutic agents. A monoterpene or sesquiterpene derivative may also be co-administered with antiviral agents, anti-inflammatory agents or antibiotics. The agents may be administered concurrently or sequentially. A monoterpene (or sesquiterpene) derivative can be administered before, during or after the administration of the other active agent(s).

The monoterpene or sesquiterpene derivative may be used in combination with radiation therapy. In one embodiment, the present invention provides for a method of treating tumor cells, such as malignant glioma cells, with radiation, where the cells are treated with an effective amount of a monoterpene derivative, such as a perillyl alcohol carbamate, and then exposed to radiation. Monoterpene derivative treatment may be before, during and/or after radiation. For example, the monoterpene or sesquiterpene derivative may be administered continuously beginning one week prior to the initiation of radiotherapy and continued for two weeks after the completion of radiotherapy. U.S. Pat. Nos. 5,587, 402 and 5,602,184.

In one embodiment, the present invention provides for a method of treating tumor cells, such as malignant glioma cells, with chemotherapy, where the cells are treated with an effective amount of a monoterpene derivative, and then exposed to chemotherapy. Monoterpene derivative treatment may be before, during and/or after chemotherapy.

The monoterpene (or sesquiterpene) derivatives of the present invention may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. As used herein, the term "nervous system tumors" refers to a condition in which a subject has a malignant proliferation of nervous system cells.

Cancers that can be treated by the present monoterpene (or sesquiterpene) derivatives include, but are not limited to, lung cancer, ear, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. U.S. Pat. No. 7,601,355.

The present invention also provides methods of treating CNS disorders, including, without limitation, primary degenerative neurological disorders such as Alzheimer's, Parkinson's, psychological disorders, psychosis and depression. Treatment may consist of the use of a monoterpene or sesquiterpene derivative alone or in combination with current medications used in the treatment of Parkinson's, Alzheimer's, or psychological disorders.

The present invention also provides a method of improving immunomodulatory therapy responses comprising the steps of exposing cells to an effective amount of a monoterpene or sisquiterpene derivative, such as a POH-TMZ-fatty acid derivative, before or during immunomodulatory treatment. Preferred immunomodulatory agents are cytokines, such interleukins, lymphokines, monokines, interfereons and chemokines.

The present composition may be administered by any method known in the art, including, without limitation, intranasal, oral, transdermal, ocular, intraperitoneal, inhalation, intravenous, ICV, intracisternal injection or infusion, subcutaneous, implant, vaginal, sublingual, urethral (e.g., urethral suppository), subcutaneous, intramuscular, intravenous, rectal, sub-lingual, mucosal, ophthalmic, spinal, intrathecal, intra-articular, intra-arterial, sub-arachinoid, bronchial and lymphatic administration. Topical formulation may be in the form of gel, ointment, cream, aerosol, etc; intranasal formulation can be delivered as a spray or in a drop; transdermal formulation may be administered via a transdermal patch or iontorphoresis; inhalation formulation can be delivered using a nebulizer or similar device. Compositions can also take the form of tablets, pills, capsules, semisolids, powders, sustained release formulations, solutions, suspensions, elixirs, aerosols, or any other appropriate compositions.

To prepare such pharmaceutical compositions, one or more of monoterpene (or sesquiterpene) derivatives may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see *Remington's Pharmaceutical Sciences*, edited by E. W. Martin (Mack Publishing Company, 18th ed., 1990). The compositions also can include stabilizers and preservatives.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition are administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer. If the composition is in the form of a gel, the composition may be rubbed onto a membrane of the patient, for example, the skin, preferably intact, clean, and dry skin, of the shoulder or upper arm and or the upper torso, and maintained thereon for a period of time sufficient for delivery of the monoterpene (or sesquiterpene) derivative to the blood serum of the patient. The composition of the present invention in gel form may be contained in a tube, a sachet, or a metered pump. Such a tube or sachet may contain one unit dose, or more than one unit dose, of the composition. A metered pump may be capable of dispensing one metered dose of the composition.

The present invention also provides the compositions as described above for intranasal administration. As such, the compositions can further comprise a permeation enhancer. Southall et al. *Developments in Nasal Drug Delivery*, 2000. The monoterpene (or sesquiterpene) derivative may be administered intranasally in a liquid form such as a solution, an emulsion, a suspension, drops, or in a solid form such as a powder, gel, or ointment. Devices to deliver intranasal medications are well known in the art. Nasal drug delivery can be carried out using devices including, but not limited to, intranasal inhalers, intranasal spray devices, atomizers, nasal spray bottles, unit dose containers, pumps, droppers, squeeze bottles, nebulizers, metered dose inhalers (MDI), pressurized dose inhalers, insufflators, and bi-directional devices. The nasal delivery device can be metered to administer an accurate effective dosage amount to the nasal cavity. The nasal delivery device can be for single unit delivery or multiple unit delivery. In a specific example, the ViaNase Electronic Atomizer from Kurve Technology (Bethell, Wash.) can be used in this invention (http://www.kurvetech.com). The compounds of the present invention may also be delivered through a tube, a catheter, a syringe, a packtail, a pledget, a nasal tampon or by submucosal infusion. U.S. Patent Publication Nos. 20090326275, 20090291894, 20090281522 and 20090317377.

The monoterpene (or sesquiterpene) derivative can be formulated as aerosols using standard procedures. The monoterpene (or sesquiterpene) derivative may be formulated with or without solvents, and formulated with or without carriers. The formulation may be a solution, or may be an aqueous emulsion with one or more surfactants. For example, an aerosol spray may be generated from pressurized container with a suitable propellant such as, dichlorodifluoromethane, trichlorofluoromethane, dichlorotetrafluoroethane, hydrocarbons, compressed air, nitrogen, carbon dioxide, or other suitable gas. The dosage unit can be determined by providing a valve to deliver a metered amount. Pump spray dispensers can dispense a metered dose or a dose having a specific particle or droplet size. As used herein, the term "aerosol" refers to a suspension of fine solid particles or liquid solution droplets in a gas. Specifically, aerosol includes a gas-borne suspension of droplets of a monoterpene (or sesquiterpene), as may be produced in any suitable device, such as an MDI, a nebulizer, or a mist sprayer. Aerosol also includes a dry powder composition of the composition of the instant invention suspended in air or other carrier gas. Gonda (1990) *Critical Reviews in Therapeutic Drug Carrier Systems* 6:273-313. Raeburn et al., (1992) *Pharmacol. Toxicol. Methods* 27:143-159.

The monoterpene (or sesquiterpene) derivative may be delivered to the nasal cavity as a powder in a form such as microspheres delivered by a nasal insufflator. The monoterpene (or sesquiterpene) derivative may be absorbed to a solid surface, for example, a carrier. The powder or microspheres may be administered in a dry, air-dispensable form. The powder or microspheres may be stored in a container of the insufflator. Alternatively the powder or microspheres may be filled into a capsule, such as a gelatin capsule, or other single dose unit adapted for nasal administration.

The pharmaceutical composition can be delivered to the nasal cavity by direct placement of the composition in the nasal cavity, for example, in the form of a gel, an ointment, a nasal emulsion, a lotion, a cream, a nasal tampon, a dropper, or a bioadhesive strip. In certain embodiments, it can be desirable to prolong the residence time of the pharmaceutical composition in the nasal cavity, for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl).

The composition containing the purified monoterpene (or sesquiterpene) can be administered by oral inhalation into the respiratory tract, i.e., the lungs.

Typical delivery systems for inhalable agents include nebulizer inhalers, dry powder inhalers (DPI), and metered-dose inhalers (MDI).

Nebulizer devices produce a stream of high velocity air that causes a therapeutic agent in the form of liquid to spray as a mist. The therapeutic agent is formulated in a liquid form such as a solution or a suspension of particles of suitable size. In one embodiment, the particles are micronized. The term "micronized" is defined as having about 90% or more of the particles with a diameter of less than about 10 µm. Suitable nebulizer devices are provided commercially, for example, by PARI GmbH (Starnberg, Germany). Other nebulizer devices include Respimat (Boehringer Ingelheim) and those disclosed in, for example, U.S. Pat. Nos. 7,568,480 and 6,123,068, and WO 97/12687. The monoterpenes (or sesquiterpenes) can be formulated for use in a nebulizer device as an aqueous solution or as a liquid suspension.

DPI devices typically administer a therapeutic agent in the form of a free flowing powder that can be dispersed in a patient's air-stream during inspiration. DPI devices which use an external energy source may also be used in the present invention. In order to achieve a free flowing powder, the therapeutic agent can be formulated with a suitable excipient (e.g., lactose). A dry powder formulation can be made, for example, by combining dry lactose having a particle size between about 1 µm and 100 µm with micronized particles of the monoterpenes (or sesquiterpenes) and dry blending. Alternatively, the monoterpene can be formulated without excipients. The formulation is loaded into a dry powder dispenser, or into inhalation cartridges or capsules for use with a dry powder delivery device. Examples of DPI devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI devices typically discharge a measured amount of therapeutic agent using compressed propellant gas. Formulations for MDI administration include a solution or suspension of active ingredient in a liquefied propellant. Examples of propellants include hydrofluoroalklanes (HFA), such as 1,1,1,2-tetrafluoroethane (HFA 134a) and 1,1,1,2,3,3,3-heptafluoro-n-propane, (HFA 227), and chlorofluorocarbons, such as $CCl_3F$. Additional components of HFA formulations for MDI administration include co-solvents, such as ethanol, pentane, water; and surfactants, such as sorbitan trioleate, oleic acid, lecithin, and glycerin. (See, for example, U.S. Pat. No. 5,225,183, EP 0717987, and WO 92/22286). The formulation is loaded into an aerosol canister, which forms a portion of an MDI device. Examples of MDI devices developed specifically for use with HFA propellants are provided in U.S. Pat. Nos. 6,006,745 and 6,143,227. For examples of processes of preparing suitable formulations and devices suitable for inhalation dosing see U.S. Pat. Nos. 6,268,533, 5,983,956, 5,874,063, and 6,221,398, and WO 99/53901, WO 00/61108, WO 99/55319 and WO 00/30614.

The monoterpene (or sesquiterpene) derivative may be encapsulated in liposomes or microcapsules for delivery via inhalation. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

The monoterpene (or sesquiterpene) derivative may also be used alone or in combination with other chemotherapeutic agents via topical application for the treatment of localized cancers such as breast cancer or melanomas. The monoterpene (or sesquiterpene) derivative may also be used in combination with narcotics or analgesics for transdermal delivery of pain medication.

This invention also provides the compositions as described above for ocular administration. As such, the compositions can further comprise a permeation enhancer. For ocular administration, the compositions described herein can be formulated as a solution, emulsion, suspension, etc. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

The monoterpene (or sesquiterpene) derivative can be given alone or in combination with other drugs for the treatment of the above diseases for a short or prolonged period of time. The present compositions can be administered to a mammal, preferably a human. Mammals include, but are not limited to, murines, rats, rabbit, simians, bovines, ovine, porcine, canines, feline, farm animals, sport animals, pets, equine, and primates.

The present invention also provides a method for inhibiting the growth of a cell in vitro, ex vivo or in vivo, where a cell, such as a cancer cell, is contacted with an effective amount of the monoterpene (or sesquiterpene) derivative as described herein.

Pathological cells or tissue such as hyperproliferative cells or tissue may be treated by contacting the cells or tissue with an effective amount of a composition of this invention. The cells, such as cancer cells, can be primary cancer cells or can be cultured cells available from tissue banks such as the American Type Culture Collection (ATCC). The pathological cells can be cells of a systemic cancer, gliomas, meningiomas, pituitary adenomas, or a CNS metastasis from a systemic cancer, lung cancer, prostate cancer, breast cancer, hematopoietic cancer or ovarian cancer. The cells can be from a vertebrate, preferably a mammal, more preferably a human. U.S. Patent Publication No. 2004/0087651. Balassiano et al. (2002) *Intern. J. Mol. Med.* 10:785-788. Thorne, et al. (2004) *Neuroscience* 127:481-496. Fernandes, et al. (2005) *Oncology Reports* 13:943-947. Da Fonseca, et al. (2008) *Surgical Neurology* 70:259267. Da Fonseca, et al. (2008) *Arch. Immunol. Ther. Exp.* 56:267-276. Hashizume, et al. (2008) *Neuroncology* 10:112-120.

In vitro efficacy of the present composition can be determined using methods well known in the art. For example, the cytoxicity of the present monoterpene (or sesquiterpene) and/or the therapeutic agents may be studied by MTT [3-(4,5-dimethylthiazol-2-yl)-2,5-diphenyl tetrazolium bromide] cytotoxicity assay. MTT assay is based on the principle of uptake of MTT, a tetrazolium salt, by metabolically active cells where it is metabolized into a blue colored formazon product, which can be read spectrometrically. *J. of Immunological Methods* 65: 55 63, 1983. The cytoxicity of the present monoterpene (or sesquiterpene) derivative and/or the therapeutic agents may be studied by colony formation assay. Functional assays for inhibition of VEGF secretion and IL-8 secretion may be performed via ELISA. Cell cycle block by the present monoterpene (or sesquiterpene) derivative and/or the therapeutic agents may be studied by standard propidium iodide (PI) staining and flow cytometry. Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to cell viability assays, apoptosis assays, and morphological assays.

The following are examples of the present invention and are not to be construed as limiting.

EXAMPLES

Example 1

Preparation of POH-TMZ-linoleate (or TMZ-POH-linoleate, TPL) triconjugate ((3-Methyl-4-oxo-3,4-dihydro-imidazo[5,1-d][1,2,3, 5]tetrazine-8-carbonyl)-octadeca-9,12-dienoyl-carbamic acid 4-isopropenyl-cyclohex-1-enylmethyl ester)

The reaction scheme is as follows:

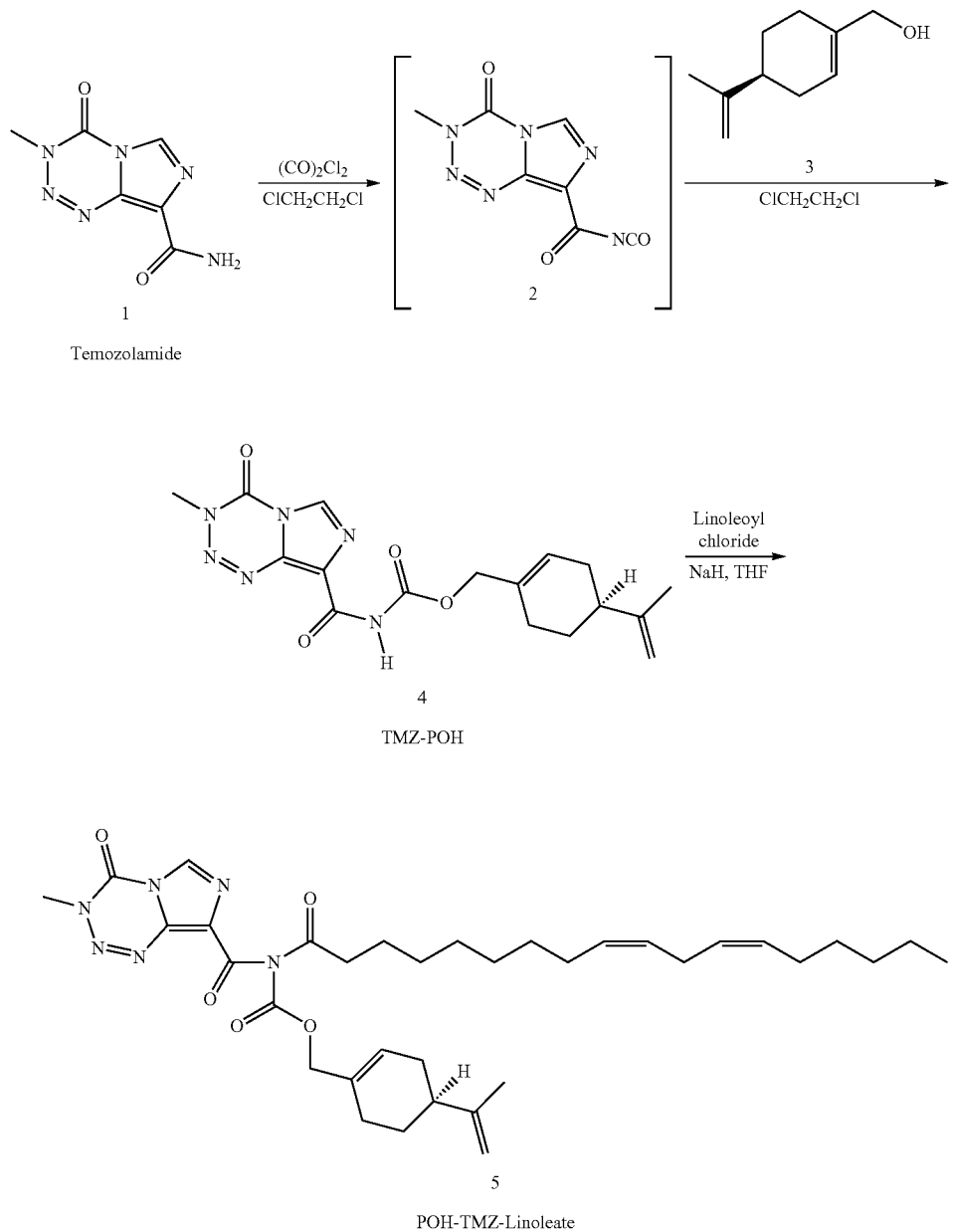

Oxalyl chloride (0.64 g, 5.04 mmol) was added slowly to a mixture of Temozolamide (Source: OChem Incorporation, Lot #9110918A; 0.5 g, 2.57 mmol) in 1,2-dichloroethane (10 mL) over a period of 2 min while maintaining the temperature at 10° C. under $N_2$. The reaction mixture was allowed to warm to room temperature and then heated to reflux for 3 h. The excess of oxalyl chloride and 1,2-dichloroethane were removed by concentration under vacuum. The resulting residue was redissolved in 1,2-dichlorethane (15 mL) and the reaction mixture was cooled to 10° C. under $N_2$. A solution of Perillyl alcohol (0.086 g, 0.56 mmol) in 1,2-dichloroethane (3 mL) was added over a period of 5 min. The reaction mixture was allowed to warm to room temperature and stirred for 14 h. 1,2-Dichloroethane was concentrated under vacuum to give a residue which was triturated with hexanes. The resulting pale-yellow solid (TMZ-POH or POH-TMZ) was filtered and washed with hexanes. Weight: 0.85 g; Yield: 89%. $^1$H-NMR (400 MHz, $CDCl_3$): δ 1.4-2.2 (m, 10H), 4.06 (s, 3H), 4.6-4.8 (m, 4H), 5.88 (br s, 1H), 8.42 (s, 1H), 9.31 (br s, 1H); MS (APCI): No molecular ion peak is observed. m/e: 314 (100%), 286.5 (17%), 136 (12%).

POH-TMZ obtained above (300 mg, 0.80 mmol) in dry THF (5.0 mL) was added to Sodium hydride (60%, 48 mg, 1.2 mmol) in dry THF (4.0 mL) at 0-5° C. The mixture was allowed to warm to 20-25° C. and stirred for 1.0 h. Linoleoyl chloride (alternatively the acid chloride of any fatty acid or carboxylic acid, R—COCl, may be used) solution (264 mg, 0.88 mmol) in dry THF was added slowly over a period of 15 min, while maintaining the temperature below 10° C. The mixture was slowly heated to 35-40° C. and stirred for 1.0 h. After confirming the completion of the reaction by TLC (20% EtOAc/Hexanes), the mixture was quenched with saturated ammonium chloride solution. The reaction mixture was extracted with ethyl acetate (2×15 mL). The combined organic layer was washed with water (25 mL), brine (10%, 25 mL) and dried over sodium sulfate. The filtered organic layer was concentrated to give an oil which was purified by column chromatography [Column dimensions: dia: 1.5 cm, height: 10 cm, silica: 230-400 mesh] and eluted with a mixture of 5% ethyl acetate/hexanes (100 mL) followed by 10% ethyl acetate/hexanes (100 mL). The 10% ethyl acetate/hexanes fractions were combined and concentrated under vacuum to give a gummy solid. Weight: 260 mg; Yield: 50%.

Example 2

Cytotoxicity of POH-TMZ-Linoleate (TPL)

Figure 2:
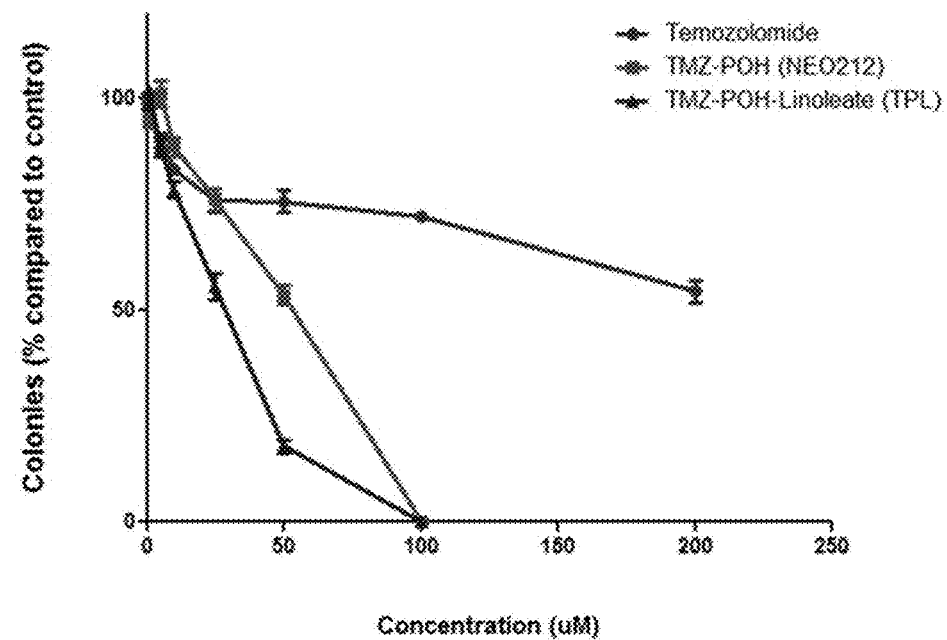
FIG. 2 is a plot showing in vitro efficacy of temozolomide (TMZ), TMZ-POH, and TPL in the treatment of MGMT positive human melanoma cells A375.

The cytotoxicity of TMZ, POH-TMZ, and POH-TMZ-Linoleate were studied by colony formation assay of A2058 and A375 melanoma cells. A2058 and A375 cells were harvested and made single cell suspension in culture medium (DMEM with 10% FBS, 1% Penicillin/Streptomycin). 500 cells/well were seeded into 12-well plate (tissue culture treated, from Olympus Plastics) pre-warmed culture medium at 37° C. The cells were cultured overnight for attachment to the plate. Then the medium was removed and replaced with fresh medium containing varied concentrations of drugs (or no drugs as a control) for further 48-hour incubation. After 48 hours treatment, the medium was aspirated and replaced with normal culture medium. 7-10 days later, the culture medium was aspirated, and the colonies formed inside the wells were washed with cold PBS once. Then the colonies were stained with 0.1% methylene blue (in methanol) for 4-6 hours. The plates were then washed and the formed colonies counted (the colonies formed with 20 cells or more are countable). The colonies count results shown in FIGS. 1 and 2 indicate that, at similar concentrations, POH-TMZ-linoleate was more effective in killing the melanoma cells than POH-TMZ, which is in turn more effective than TMZ.

Example 3

In Vivo Tumor Growth Inhibition by POH-TMZ-Linoleate (TPL)

Figure 3A:
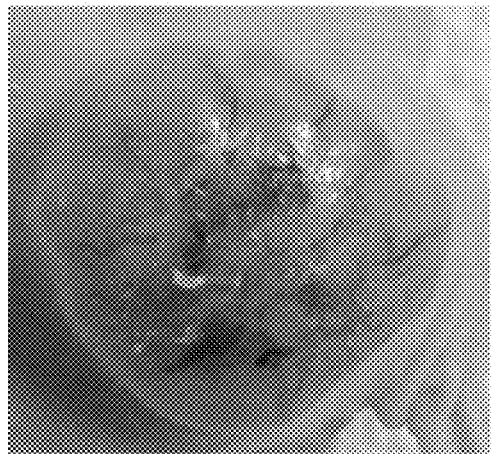
FIG. 3A is an image of a tumor formed on the skin of a nude mouse due to subcutaneously injected melanoma cells.
Figure 3B:
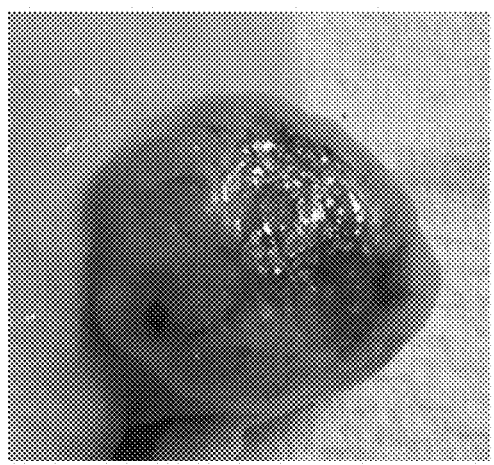
FIG. 3B is an image of the tumor depicted in FIG. 3A after being treated with TPL for 14 days.

Inhibition of tumor growth by POH-TMZ-linoleate was studied in nude mice. Nude mice were injected subcutaneously with $2 \times 10^6$ human melanoma tumor cells, A2058. The melanoma cells were allowed to form a palpable nodule in the mice. When the tumor size reached 1.0-1.5 cm in diameter in any dimension, a control mouse was treated topically with a vehicle (10% DMSO in 45% Glycerol+45% ethanol), and a test mouse was topically treated with TPL (50 mM TPL working solution was reconstituted in 45% Glycerol+45% Ethanol, and 100 μl (25 mg/kg) was applied topically on the skin which covers the whole tumor). The control mouse and the test mouse were both treated twice daily for 14 days. It was observed that the tumor of the test mouse developed a hard surface after 14 days of treatment (FIG. 3B), with reduced vascularization compared with the tumor before the treatment (FIG. 3A).

Figure 4A:
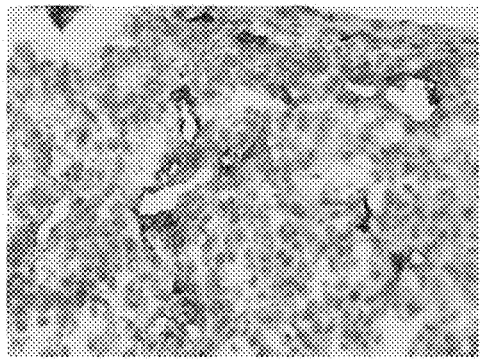
FIGS. 4A-4C are example micrographs of the tissue stained for visualization of CD31 marker expression obtained from a tumor formed on the skin of a nude mouse due to subcutaneously injected melanoma cells, where the mouse had been treated by a vehicle for 14 days.
Figure 4B:
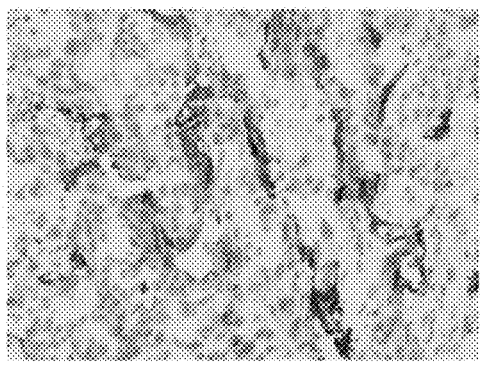
Figure 4C:
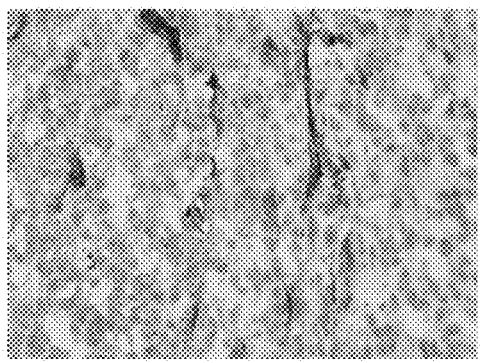
Figure 4D:
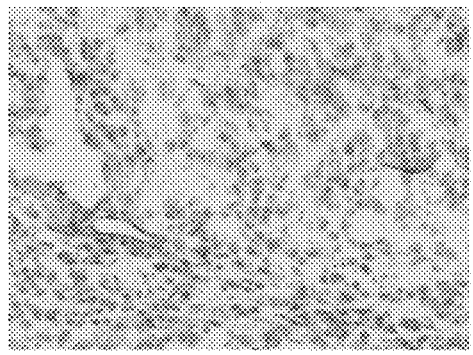
FIGS. 4D-4F are example micrographs of the tissue stained for visualization of CD31 marker expression obtained from a nodule formed on the skin of a nude mouse due to subcutaneously injected melanoma cells, where the mouse had been treated by TPL for 14 days.
Figure 4E:
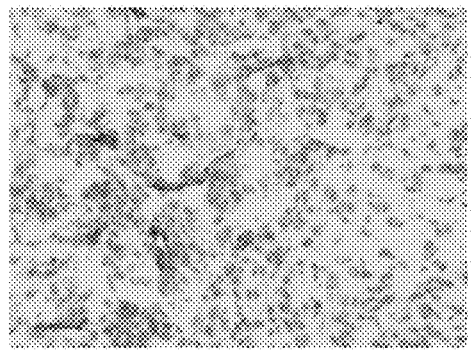
Figure 4F:
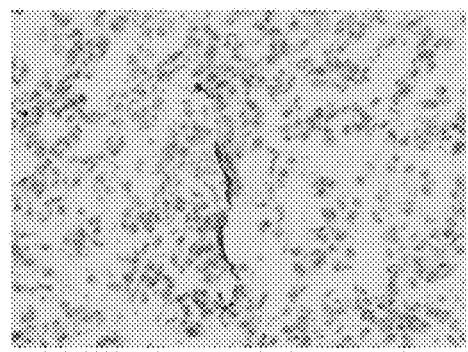
Figure 5:
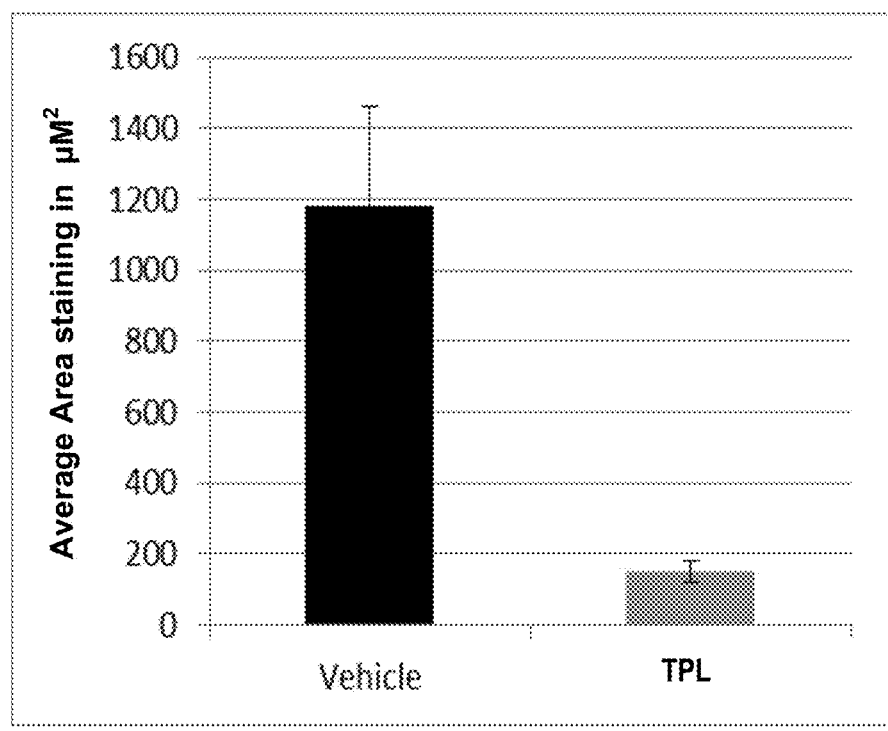
FIG. 5 is a plot comparing the average area representing CD31 marker expression in a nodule formed on the skin of a nude mouse due to subcutaneously injected melanoma cells which had been treated with TPL for 14 days with that of a control mouse treated with a vehicle.

After the 14 days of treatment the mice were sacrificed, the tumor removed, sectioned at 8 μm, fixed with acetone, and stored at −20° C. For histological analysis, the tissues were blocked with sea block and stained with the primary antibody Rat anti Mouse (1:50) overnight following which secondary biotinylated goat anti rat antibody (1:200) was added for 45 minutes, washed and avidin biotin complex, ABC elite was added for 30 minutes, washed and then stained with AEC and counter stained with hematoxylin. Such staining was used to evaluate the endothelial marker CD31 expression, which is representative of the amounts of blood vessels in the tumor. Staining images were captured at 40× under optical microscope. A visual inspection of the stained tissues showed that the tumor angiogenesis was much lower in the TPL-treated mouse (FIGS. 4D-4F) than that in the vehicle-treated mouse (FIGS. 4A-4C). The histological analysis results were further quantified using ImageJ software by measuring the average area of staining in the tumors of the test mouse after TPL treatment and the control mouse, where the average area of staining was calculated based on the red precipitate of the stain in $\mu m^2$. From FIG. 5, it can be seen that the average area of staining is much smaller in the tumor of the test mouse than that in the control mouse. These comparisons demonstrate the efficacy of TPL in treating melanoma.

The scope of the present invention is not limited by what has been specifically shown and described hereinabove. Variations, modifications and other implementations of what is described herein will occur to those of ordinary skill in the art without departing from the spirit and scope of the invention.

What is claimed is:

1. A compound of the Formula I;

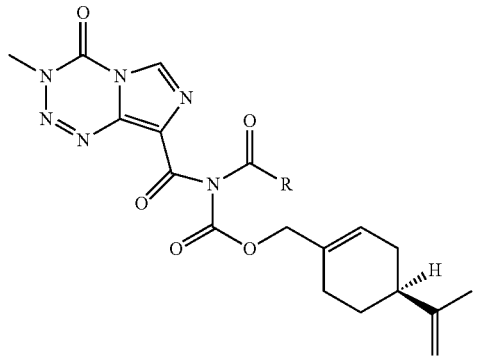

wherein R is selected from the group consisting of a $C_4$ to $C_{28}$ linear or branched alkyl, linear or branched $C_4$ to $C_{28}$ alkeneyl and a linear or branched $C_4$ to $C_{28}$ alkynyl group; or a pharmaceutically acceptable salt thereof.

2. The compound according to claim 1 wherein R is a $C_4$ to $C_{28}$ linear or branched alkeneyl containing 1, 2, 3, 4 or 5 double bonds or a linear or branched $C_4$ to $C_{28}$ alkynyl group containing 1, 2, 3, 4 or 5 triple bonds.

3. The compound according to claim 1 of the Formula II;

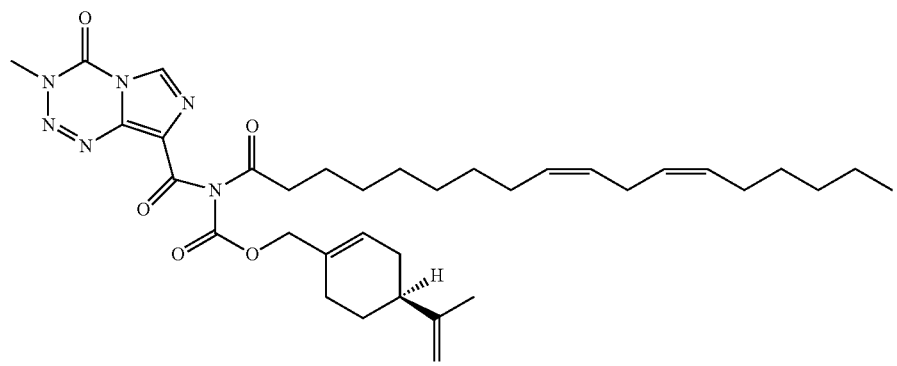 [SMILES: C=C(C)[C@@H]1CC=C(COC(=O)N(C(=O)CCCCCCC/C=C\C/C=C\CCCCC)C(=O)c2ncn3c(=O)n(C)nnc23)CC1]

or a pharmaceutically acceptable salt thereof.

4. A method of treating melanoma in a mammal, comprising the step of administering to the mammal a therapeutically effective amount of the compound according to claim 1, 2 or 3.

5. The method of claim 4, wherein the compound is administered topically.

6. A pharmaceutical composition comprising a compound according to claim 1, 2 or 3.

7. A compound of the Formula III;

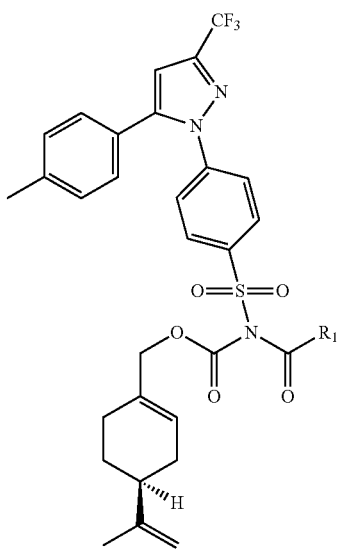

wherein $R_1$ is selected from a $C_4$ to $C_{28}$ linear or branched alkyl, linear or branched $C_4$ to $C_{28}$ alkeneyl or a linear or branched $C_4$ to $C_{28}$ alkynyl group; or a pharmaceutically acceptable salt thereof.

8. The compound according to claim 7 wherein $R_1$ is a $C_4$ to $C_{28}$ linear or branched alkeneyl containing 1, 2, 3, 4 or 5 double bonds or a linear or branched $C_4$ to $C_{28}$ alkynyl group containing 1, 2, 3, 4 or 5 triple bonds.

9. The compound according to claim 7 of the Formula IV; or a pharmaceutically acceptable salt thereof

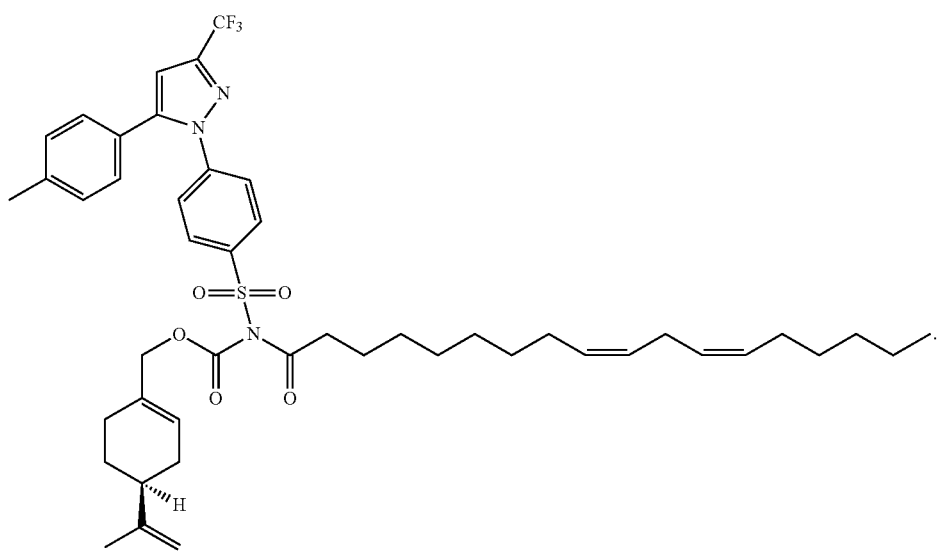 [SMILES: C=C(C)[C@@H]1CC=C(COC(=O)N(C(=O)CCCCCCC/C=C\C/C=C\CCCCC)S(=O)(=O)c2ccc(-n3nc(C(F)(F)F)cc3-c3ccc(C)cc3)cc2)CC1]

10. A pharmaceutical composition comprising a compound according to claim 7, 8 or 9.

11. A process for making a compound of the Formula I

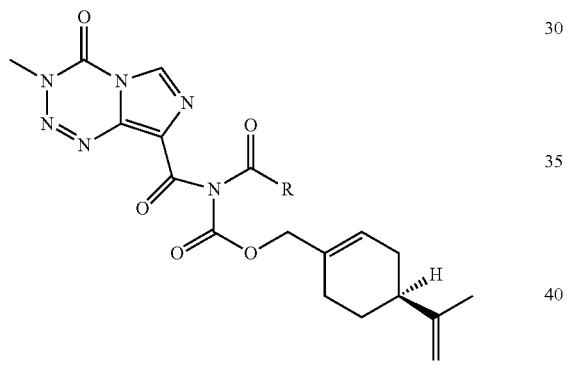

comprising the steps of a) reacting Temozolamide with oxalyl chloride in a halogenated solvent to give the isocyanate of Temozolamide Formula A

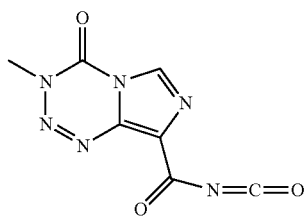 [SMILES: Cn1nnc2c(C(=O)N=C=O)ncn2c1=O]

b) reacting the isocyanate of Temozolamide with perillyl alcohol in a halogenated solvent to afford a compound of Formula B

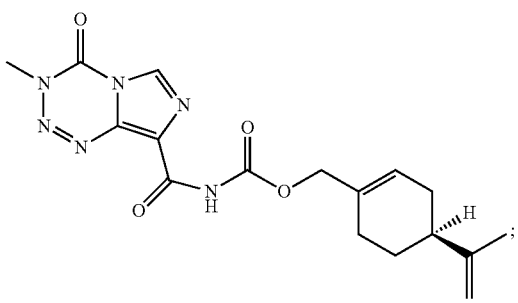 [SMILES: C=C(C)[C@@H]1CC=C(COC(=O)NC(=O)c2ncn3c(=O)n(C)nnc23)CC1]

c) reacting the compound of Formula B with an acid chloride of the Formula C

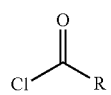

wherein R is selected from the group consisting of a $C_4$ to $C_{28}$ linear or branched alkyl, linear or branched $C_4$ to $C_{28}$ alkeneyl containing 1, 2, 3, 4, or 5 double bonds or a linear or branched $C_4$ to $C_{28}$ alkynyl group; containing 1, 2, 3, 4 or 5 triple bonds in the presence of a base in an ethereal solvent to afford a compound of the Formula I.

12. The process according to claim 11 wherein the halogenated solvent is 1,2 dichloroethane.

13. The process according to claim 11 wherein the acid chloride is linoleic acid chloride.

14. The process according to claim 11 wherein the base is NaH.

15. The process according to claim 11 wherein the ethereal solvent is THF.

* * * * *

UNITED STATES PATENT AND TRADEMARK OFFICE
CERTIFICATE OF CORRECTION

| | | |
|---|---|---|
| PATENT NO. | : 9,522,918 B2 | Page 1 of 1 |
| APPLICATION NO. | : 15/041743 | |
| DATED | : December 20, 2016 | |
| INVENTOR(S) | : Chen et al. | |

It is certified that error appears in the above-identified patent and that said Letters Patent is hereby corrected as shown below:

On the Title Page

(72) Inventors:
Change "Pupalli" to --Puppali--

Signed and Sealed this
Ninth Day of May, 2023

Katherine Kelly Vidal
*Director of the United States Patent and Trademark Office*